(12) United States Patent
Figueroa Pérez et al.

(10) Patent No.: US 9,237,764 B2
(45) Date of Patent: Jan. 19, 2016

(54) PRODUCTION OF 6'-O-SIALYLLACTOSE AND INTERMEDIATES

(75) Inventors: Ignacio Figueroa Pérez, Miami, FL (US); Ferenc Horváth, Pilisszentkereszt (HU); Gyula Dekany, Sinnamon Park (AU); Károly Ágoston, Telki (HU); Ágnes Ágoston, Telki (HU); István Bajza, Debrecen (HU); Julien Boutet, La Plaine sur Mer (FR); Markus Hederos, Svedala (SE); Piroska Kovács-Pénzes, Jászberény (HU); Lars Kröger, Hamburg (DE); Christoph Röhrig, Mühlingen (DE); Andreas Schroven, Barssel (DE); Ioannis Vrasidas, Thessaloniki (GR); Christian Risinger, Rottweil (DE)

(73) Assignee: Glycom A/S, Kongens Lyngby (DK)

( * ) Notice: Subject to any disclaimer, the term of this patent is extended or adjusted under 35 U.S.C. 154(b) by 502 days.

(21) Appl. No.: 13/579,738

(22) PCT Filed: Feb. 21, 2011

(86) PCT No.: PCT/DK2011/050052
§ 371 (c)(1),
(2), (4) Date: Sep. 19, 2012

(87) PCT Pub. No.: WO2011/100979
PCT Pub. Date: Aug. 25, 2011

(65) Prior Publication Data
US 2013/0035481 A1 Feb. 7, 2013

(30) Foreign Application Priority Data

Feb. 19, 2010 (DK) .................................. 2010 70061

(51) Int. Cl.
| | | |
|---|---|---|
| C07H 1/00 | (2006.01) | |
| C07H 3/04 | (2006.01) | |
| C07H 5/04 | (2006.01) | |
| C07H 5/10 | (2006.01) | |
| A23L 1/308 | (2006.01) | |
| C07H 3/06 | (2006.01) | |
| C07H 15/18 | (2006.01) | |
| A61K 31/702 | (2006.01) | |
| C07H 13/04 | (2006.01) | |
| A23L 1/30 | (2006.01) | |

(52) U.S. Cl.
CPC . *A23L 1/308* (2013.01); *A23L 1/30* (2013.01); *A61K 31/702* (2013.01); *C07H 3/06* (2013.01); *C07H 13/04* (2013.01); *C07H 15/18* (2013.01)

(58) Field of Classification Search
CPC .......... C07H 3/06; C07H 13/04; C07H 15/18; A61K 31/702
USPC .......... 536/123.1, 123.13, 55.3, 4.1, 18.7, 54; 514/54
See application file for complete search history.

(56) References Cited

U.S. PATENT DOCUMENTS

| | | |
|---|---|---|
| 6,288,222 B1 | 9/2001 | Roth et al. |
| 6,623,954 B1 | 9/2003 | Spade et al. |
| 2002/0064836 A1 | 5/2002 | Koizumi et al. |
| 2009/0082307 A1 | 3/2009 | Samain et al. |

FOREIGN PATENT DOCUMENTS

| | | |
|---|---|---|
| EP | 0254105 A2 | 1/1988 |
| EP | 0479769 | 4/1992 |
| WO | WO2007090894 | 8/2007 |
| WO | 2010/116317 | 10/2010 |

OTHER PUBLICATIONS

Crich et al.( J. Org. Chem. 2007, 72, 3581-3584).*
Muller et al. (Tetrahedron Letters (1998), 39(7), 509-512).*
Newburg D. S. et al., "Human Milk Glycans Protect Infants Against Enteric Pathogens" Annu. Rev. Nutr. vol. 25; pp. 37-58, 2005.
Kunz C. et al., "Biological Functions of Oligosaccharides in Human Milk", Acta Pædiatr. vol. 82, pp. 903-912, 1993.
Furuhata K. et al., "Studies on Sialic Acids. V. Synthesis of α- and β-D-Neu5Acp-(2→6)-lactose", Chem. Pharm. Bull. vol. 34, No. 7; pp. 2725-2731, 1986.
Pozsgay V. et al., "A Novel Approach to N-acetyl-neuraminic cid-containing Oligosaccharides. Synthesis of a Glycosyl Donor Derivative of α-N-acetyl-D-neuraminyl-(2+6)-D-galactose", J. Carbohydrate Chemistry, vol. 6, No. 1; pp. 41-55, 1987. Marcel Dekker, Inc.
Liu Y. et al., "Neoglycolipid Probes Prepared via Oxime Ligation for Microarray Analysis of Oligosaccharide-protein Interactions", Chemistry & Biology. vol. 14; pp. 847-859, 2007. Elsevier Ltd.

(Continued)

*Primary Examiner* — Shaojia Anna Jiang
*Assistant Examiner* — Michael C Henry
(74) *Attorney, Agent, or Firm* — McHale & Slavin, P.A.

(57) ABSTRACT

The present invention relates to a method for preparation of the trisaccharide 6'-O-sialyllactose (formula (I)) or salts thereof as well as intermediates in the synthesis and for the use of 6'-O-sialyllactose salts in pharmaceutical or nutritional compositions.

formula (I)

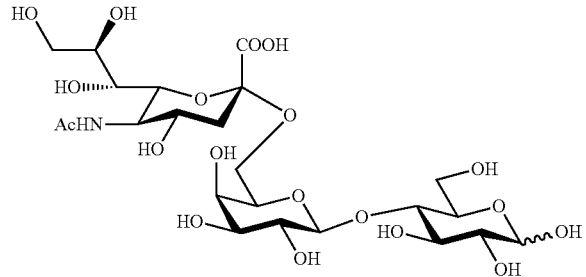

7 Claims, No Drawings

(56) References Cited

OTHER PUBLICATIONS

Rencurosi A. et al., "Human Milk Oligosaccharides: an Enzymatic Protection Step Simplifies the Synthesis of 3'- and 6'-O-sialyllactose and their Analogues", Carbohydrate Research 337; pp. 473-483. 2002. Elsevier Science Ltd.

Thomas R. L. et al., "Silver Zeolite—Effective Catalyst for the regio-Stereoselective Formation of the Neu5Acα2→6 Glycosyl Linkage—Synthesis of Several Sialosaccharides", Tetrahedron Letters, vol. 31, No. 20; pp. 2825-2828, 1990. Pergamon Press plc.

Pazynina G. et al., "Simple Stereoselective Synthesis of α2-6 sialooligosaccharides", Tetrahedron Lettetrs, vol. 43; pp. 8011-8013, 2002. Elsevier Science Ltd.

Matsuoka K. et al., "Synthesis of a Useful Lauryl Thioglycoside of Sialic Acid and its Preparation", Tetrahedron Letters, vol. 45; pp. 9383-9386. 2004. Elsevier Ltd.

Simon E. S. et al., "Synthesis of CMP-NeuAc from N-Acetylglucosamine: Generation of CTP from CMP Using Adenylate Kinase", J. Am. Chem. Soc., vol. 110, No. 21; pp. 7159-7163, 1988. American Chemical Society.

Simon E. S. et al. "Preparation of Cytidine 5'-Monophospho-N-Acetylneuraminic Acid and Uridine 5'-Diphosphoglucuronic Acid: Syntheses of α-2, 6-Sialyllactosamine, α-2, 6-Sialyllactose, and Hyaluronic Acid", Methods in Enzymology, vol. 179; pp. 275-287, 1989. Academic Press, Inc.

Ajisaka K. et al. "Regioselective transglycolisation in the synthesis of oligosaccharides: comparison of beta-galactosidases and sialidases of various origins", Carbohydrate Research 259; pp. 103-115, 1994; Elsevier Science B.V.

Tanaka H. et al., "A System for Sialic Acid Transfer by Colominic Acid and a Sialidase that Preferentially Hydrolyzes Sialyl α-2,8 Linkages", Biosci. Biotech. Biochem. vol. 59, No. 4; pp. 638-643, 1995.

Schmidt D. et al., "Sialidase-catalyzed Transsialylation Using Polymer-supported Solution-phase Techniques", Chem. Comm., pp. 1919-1920, 2000. The Royal Society of Chemistry.

Maru I. et al., "Synthesis of Sialyllactose from N-acetylneuraminic Acid and Lactose by a Neuraminidase from Arthrobacter Ureafaciens", Biosci. Biotech. Biocem. vol. 56 No. 10; pp. 1557-1561. 1992.

Groenberg G. et al., "Isolation of Monosialylated Oligosaccharides from Human Milk and Structural Analysis of Three new Compounds", Carbohydrate Research 191; pp. 261-278. 1989. Elsevier Science Publishers B.V.—Amsterdam.

Furuhata K. et al., "Chemistry of N-Acetylneuraminic Acid (Neu5AC)", Trends Glycoscience and Glycotechnology, vol. 16, No. 89; pp. 143-169, 2004.

Ress D. K. et al., "Sialic Acid Donors: Chemical Synthesis and Glycolsylation", Current Organic Synthesis, vol. 1; pp. 31-46, 2004. Bentham Science Publishers Ltd.

Chen X. et al. "Advances in the Biology and Chemistry of Sialic Acids", ACS Chemical Biology, vol. 5, No. 2; pp. 163-176, 2010.

Database Registry, RN-35890-39-2, STN entry date Nov. 16, 1984.
Database Registry, RN-157574-76-0, STN entry date Sep. 9, 1994.
Database Registry, RN-70472-20-7, STN entry date Nov. 16, 1984.

Ogura H. et al., "Synthesis of 9-O-acyl- and 4-O-acetyl-sialic acids", Carbohydrate Research, vol. 167; pp. 77-86, 1987. Elsevier Science Publishers B.V.—Amsterdam.

Angus, D. et al, "The Synthesis of Biotinylated Carbohydrates as Probes for Carbohydrate-Recognizing Proteins", Bioorganic & Medicinal Chemistry, vol. 8, pp. 2709-2718, (2000).

Cao, H. et al, "Parallel chemoenzymatic synthesis of sialosides containing a C5-diversified sialic acid", Bioorganic & Medicinal Chemistry Letters, vol. 19, pp. 5869-5871, (2009).

Kuhn, R. et al, "Bestimmung der Bindungsstelle von Sialinsaureresten in Oligosacchariden mit Hilfe von Perjodat", Chem. Ber., vol. 98, pp. 395-413, (1965) Abstract and full reference.

Paulsen, H. et al, Synthese Der Tetra- Und Trisaccharid-Sequenzen Von Asialo-GM1 Und-GM2. Lenkung Der Regioselektivitat Der Glycosidierung Von Lactose, Carbohydrate Research, vol. 137, pp. 39-62, (1985).

Rexford, T. et al, "Silver Zeolite—Effective Catalyst For The Regio-Stereoselective Formation Of The Neu5Aca2+6 Gylcosyl Linkage—Synthesis Of Several Sialosaccharides", Tetrahedron Letters, 31:20:2825-2828, (1990).

* cited by examiner

PRODUCTION OF 6'-O-SIALYLLACTOSE AND INTERMEDIATES

CROSS-REFERENCE TO RELATED APPLICATIONS

This application is a §371 national stage entry of International Application No. PCT/DK0211/050052, filed Feb. 21, 2011, which claims priority to DK Patent Application No. 2010 70061 filed Feb. 19, 2010, the entire contents of which are incorporated herein by reference.

FIELD OF THE INVENTION

The present invention provides novel oligosaccharides and derivatives thereof, and furthermore methods for the preparation of these oligosaccharides, especially in large scale.

BACKGROUND OF THE INVENTION

During the past decades the interest for preparation and commercialization of human milk oligosaccharides has been increasing steadily. The importance of human milk oligosaccharides is directly linked to their unique biological activities such as antibacterial, antiviral, immune system and cognitive development enhancing activities [1].

Sialylated human milk oligosaccharides such as disialyl-lacto-N-tetraose, 3'-O-sialyl-3-O-fucosyllactose, 6'-O-sialyllactose, 3'-O-sialyllactose, 6'-O-sialylated-lacto-N-neotetraose, 3'-O-sialylated-lacto-N-tetraose etc. are major components of human milk.

Among the above listed sialylated human milk oligosaccharides the sialic acid residue is always linked to the terminal 3'-O- and/or 6'-O— position(s) of D-galactose or to 6-O-positions of non terminal sugar residues via α-glycosidic linkages.

To date, access to large volumes of sialylated human milk oligosaccharides has not been possible by using isolation, biotechnology and synthetic methodologies. The chemical synthesis of sialylated human milk oligosaccharides is one of the most challenging fields of carbohydrate chemistry due to the nature of sialic acid donors themselves. In general, stereoselective glycosylations are achieved via neighbouring group participations but the lack of a substituent at C-3 position of sialic acid prevents such an option. Thus, stereoselective sialylation has to be achieved via careful selection of a sialic acid donor—acceptor match, kinetic and solvent effects. Furthermore, the presence of the carboxylic moiety at the anomeric position of sialic acid also creates unfavoured steric and electronic effects for stereoselective α-sialylations. The strong electron withdrawing effect of the carboxylic group initiates potential side reactions during the glycosylation via β-elimination.

Both the biological importance and the synthetic difficulties of sialylated oligosaccharides can be demonstrated via reviewing the background art of one of the simplest sialylated human milk oligosaccharides called 6'-O-sialyllactose (6'-SL, O—(N-acetyl-α-neuraminosyl)-(2→6)-O-β-D-galactopyranosyl-(1→4)-D-glucose, Scheme 1).

Scheme 1. The structure 6'-O-sialyllactose

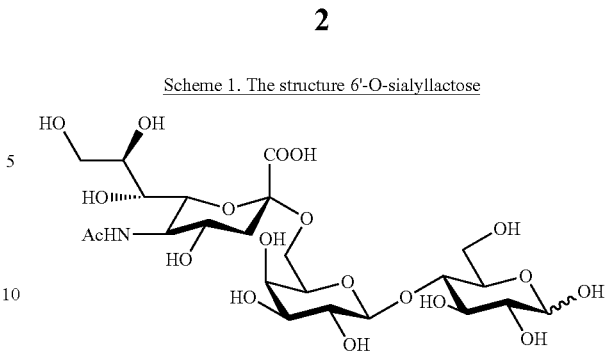

6'-O-Sialyllactose is one of the sialylated human milk oligosaccharides found in high concentration in mother's milk. Several biological roles of 6'-O-sialyllactose such as its prebiotic, antibacterial, antiviral, immune system and cognitive development enhancing etc. effects [1] have been demonstrated. These important features make 6'-SL an attractive target for large scale production and product development for the nutritional and therapeutic industries. 6'-O-Sialyllactose has been synthesised by chemical [2], enzymatic [3] and biotechnological [4] methodologies or it has been isolated from natural sources [5]. However, these methodologies have not been attractive for scale-up due to lack of efficient purification methodologies, use of expensive and toxic reagents and the involvements of many synthetic steps.

Several chemical synthetic methods have been developed towards 6'-O-sialyllactose [2a-c], Na, K, Mg and Ca salts thereof [2d, e] or intermediates thereof [2f-j]. In summary, these strategies gives 6'-O-sialylated lactose via stereoselective 6'-O-sialylation of either 4',6'-sugar diols or 6'-sugar alcohols using glycosylhalide, thioglycoside or diethylphosphite donor activations. The use of either very expensive or very toxic chemicals for the sialylation such as mercury cyanide, mercury bromide and silver carbonate is one of the reasons that make these methodologies less attractive for scale-up studies and production. Non efficient stereocontrol and/or yields likewise make(s) the strategies less suitable for large scale technology developments. Additionally, severe purification difficulties characterize all the listed synthetic strategies.

In case of enzymatic production of 6'-O-sialyllactose glycosyltransferases and sialidases are the preferred enzymes used [3]. These complex enzymatic systems represent very expensive methodologies for scale up productions of 6'-O-sialyllactose. Similarly, sialidases could not be used successfully in large scale production methodologies due to their lack of regio- and stereoselectivity. Low yields and difficult purification protocols are likewise a hindrance for industrial scale technology developments.

The isolation of 6'-SL from human and other mammals' milk is rather difficult even in milligram quantities due to the presence of a large number of similar oligosaccharides. To date, only analytical HPLC methodologies have been developed for the isolation of 6'-SL from natural sources [5].

Some biotechnological methodologies are also described using genetically modified bacteria, yeast or other micro organisms [4]. Such methodologies have serious drawbacks in regulatory processes due to limiting commercialisation opportunities.

The present invention represents the first commercial approach suitable for industrial manufacture of 6'-O-sialyllactose and other sialylated bioactive oligosaccharides. The successful strategy is based upon the introduction of novel sialic acid donor-acceptor pairs, novel sialic acid donors, novel diol-type lactose acceptors, relevant crystalline intermediates, the use of cheap and non-toxic activators and robust purification methodologies.

SUMMARY OF THE INVENTION

The first aspect of the present invention relates to a method for the preparation of 6'-O-sialyllactose or a salt thereof, comprising the steps of:

a) reaction of an acceptor of general formula 3

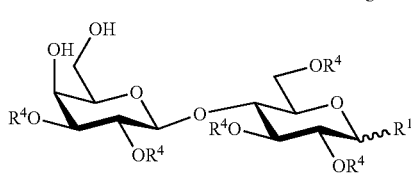

general formula 3 wherein R¹ is —OR², which R² is a group removable by catalytic hydrogenation, or R¹ is —SR³, which R³ is selected from optionally substituted alkyl, optionally substituted aryl and optionally substituted benzyl, or R¹ is —NH—C(R")=C(R')$_2$, wherein each R' independently of each other is an electron withdrawing group selected from —CN, —COOH, —COO-alkyl, —CO-alkyl, —CONH$_2$, —CONH-alkyl and —CON(alkyl)$_2$, or wherein the two R'-groups is linked together and represent —CO—(CH$_2$)$_{2-4}$—CO— and thus form with the carbon atom to which they are attached a 5-7 membered cycloalkan-1,3-dion, in which dion any of the methylene groups is optionally substituted with 1 or 2 alkyl groups, and R" is H or alkyl, R⁴ is selected from optionally substituted acyl and benzyl substituted by 1-3 methoxy group(s), with a donor of general formula 4

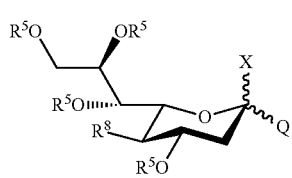

general formula 4 wherein R⁵ is optionally substituted acyl,
R⁸ is selected from —NHAc and —NAc$_2$,
Q is COO-alkyl, which alkyl is optionally substituted, and
X is leaving group,
to yield a compound of general formula 2

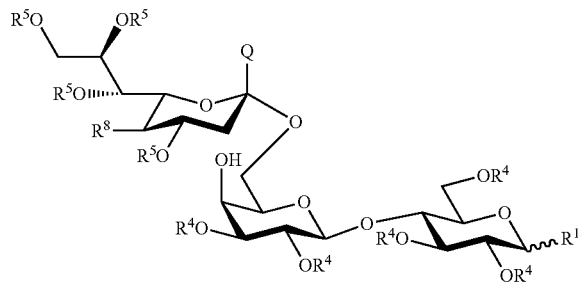

general formula 2 wherein R¹, R⁴, R⁵, R⁸ and Q are as defined above, b) deprotection of a compound of general formula 2 to give a compound of general formula 1 or salts thereof

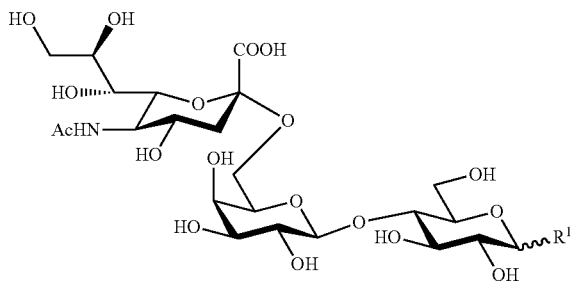

general formula 1 wherein R¹ is as defined above, and c) subsequently converting the compound of general formula 1 or salts thereof into 6'-O-sialyllactose or salts thereof.

The second aspect of the present invention provides 6'-O-sialyllactose Zn$^{2+}$ salt.

The third aspect of the present invention relates to 6'-O-sialyllactose organic salts.

The fourth aspect of the present invention provides novel 6'-O-sialyllactose salts according to the second and third aspects for use as nutritional additive.

The fifth aspect of the present invention relates to novel 6'-O-sialyllactose salts according to the second and third aspects for use as pharmaceutical additive.

The sixth aspect of the present invention provides a nutritional composition comprising one or more 6'-O-sialyllactose salts according to the second and third aspects.

The seventh aspect of the present invention relates to a pharmaceutical composition comprising one or more 6'-O-sialyllactose salts according to the second and third aspects.

The eighth aspect of the present invention provides compounds of general formula 1A

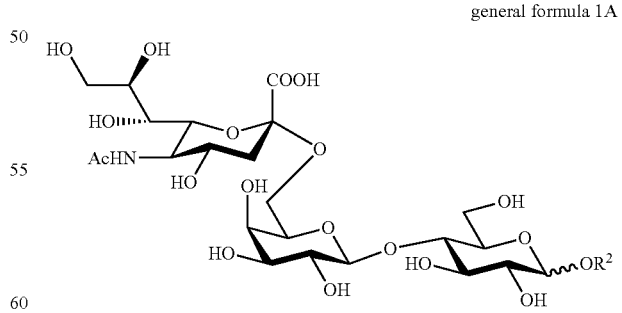

general formula 1A wherein R² is a group removable by catalytic hydrogenation, preferably benzyl, 4-methylbenzyl, 4-chlorobenzyl and 1-naphthylmethyl and OR² is in β.

The ninth aspect of the present invention relates to compounds of general formula 1B

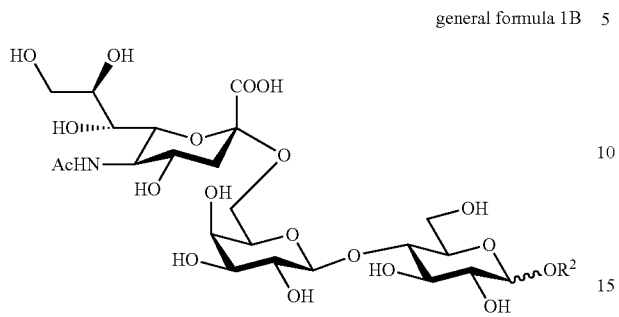

general formula 1B wherein $R^2$ is a group removable by catalytic hydrogenation,
in salt form selected from the $Zn^{2+}$, $K^+$, $Ca^{2+}$, $Mg^{2+}$, $Ba^{2+}$, $Fe^{2+}$, $Mn^{2+}$, $Cu^{2+}$ and organic salts.

The tenth aspect of the present invention provides a compound of general formula 2A

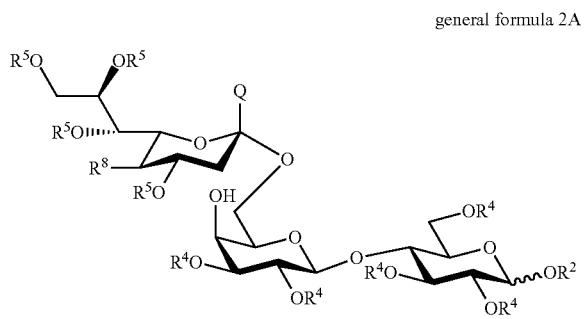

general formula 2A wherein $R^2$ is a group removable by catalytic hydrogenation,
$R^4$ and $R^5$ are independently from each other optionally substituted acyl,
$R^8$ is selected from —NHAc and —NAc$_2$, and
Q is —COO-alkyl, which alkyl is optionally substituted.

The eleventh aspect of the present invention relates to a compound of general formula 2C

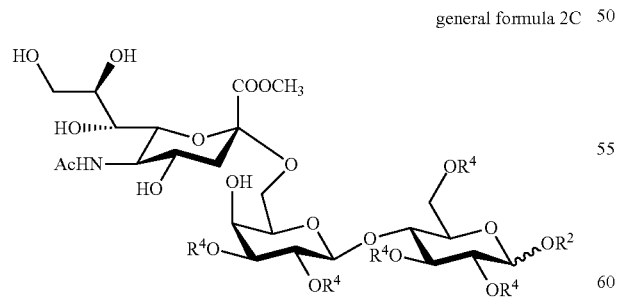

general formula 2C wherein —$OR^2$ is in β, $R^2$ is a group removable by catalytic hydrogenation, preferably benzyl, 4-methylbenzyl, 4-chlorobenzyl and 1-naphthylmethyl, and
$R^4$ is selected from isobutyryl, pivaloyl and optionally substituted benzoyl, preferably benzoyl.

The twelfth aspect of the present invention provides a compound of general formula 2D

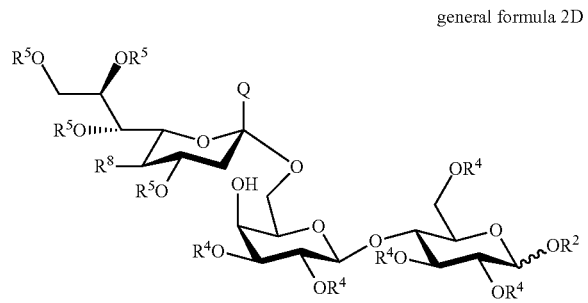

general formula 2D wherein $R^2$ is a group removable by catalytic hydrogenation,
$R^4$ is selected from benzyl substituted by 1-3 methoxy group(s) and H,
$R^5$ is selected from optionally substituted acyl and H,
$R^8$ is selected from —NHAc and NAc$_2$, and
Q is selected from —COO-alkyl, which alkyl is optionally substituted and —COOH in either protonated or deprotonated form,
provided that if Q is —COOH in either protonated or deprotonated form and $R^8$ is —NHAc, then both $R^4$ and $R^5$ cannot be H simultaneously.

The thirteenth aspect of the present invention relates to a compound of general formula 4A or 4B

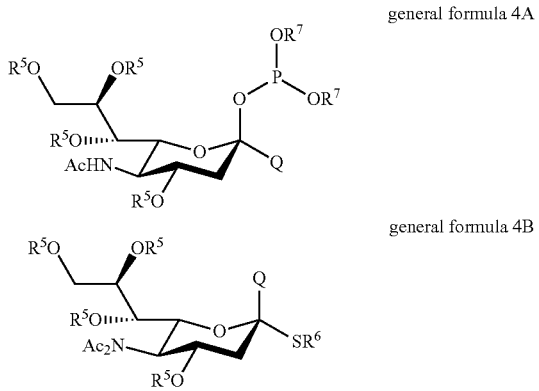

general formula 4A general formula 4B wherein $R^5$ is optionally substituted acyl, preferably acetyl,
$R^6$ is selected from $C_{2-6}$ alkyl, $C_{3-6}$ cycloalkyl and optionally substituted benzyl, preferably from ethyl, isopropyl, t-butyl, benzyl and cyclohexyl,
$R^7$ is substituted benzyl, preferably 4-chlorobenzyl or 4-bromobenzyl, and
Q is —COO-alkyl, which alkyl is optionally substituted, preferably —COOMe.

The fourteenth aspect of the present invention provides a compound of general formula 4C for use as sialyl donor

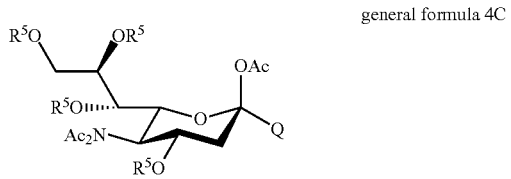

general formula 4C wherein R⁵ is optionally substituted acyl, preferably acetyl and Q is —COO-alkyl, which alkyl is optionally substituted, preferably —COOMe.

The fifteenth aspect of the present invention relates to a compound of general formula 3A

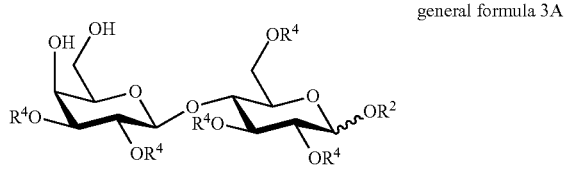

general formula 3A wherein R² is a group removable by catalytic hydrogenation, and R⁴ is selected from benzyl substituted by 1-3 methoxy group(s) and optionally substituted acyl provided that acetyl is excluded.

DETAILED DISCLOSURE OF THE INVENTION

Throughout the present description, the term "alkyl", either alone or when attached to another atom or group, means a linear or branched hydrocarbon group with 1-6 carbon atoms, like methyl, ethyl, n-propyl, i-propyl, n-butyl, i-butyl, s-butyl, t-butyl, etc.

"Cycloalkyl" means cyclic hydrocarbon residue with 3-6 carbon atoms like cyclopropyl, cyclobutyl, cyclopentyl and cyclohexyl.

In the present application the term "aryl" refers to homoaromatic groups like phenyl or naphthyl. Preferably, aryl means phenyl.

In the present description, the term "acyl" represent an R—C(=O)—, wherein R may be H, alkyl or aryl, like formyl, acetyl, propionyl, butyryl, pivaloyl, benzoyl, etc. The alkyl and aryl residues both may be substituted.

For the purpose of this specification with claims, the term "optionally substituted" means that the group in question may either carry a substituent or may be unsubstituted.

For the purpose of this specification with claims, the term "substituted" means that the group in question is substituted with a group which modifies the general chemical characteristics of the chain or ring. The substituents can be used to modify characteristics of the molecule as a whole, such as stability, solubility, and ability to form crystals. The person skilled in the art will be aware of other suitable substituents of a similar size and charge characteristics, which could be used as alternatives in a given situation.

More generally in connection with the terms "alkyl", "cycloalkyl", "aryl" and "acyl" the term "optionally substituted" is intended to mean that the group in question may be substituted one or several times, preferably 1-5 times, more preferably 1-3 times with group(s) selected from the group consisting of alkyl (only for cycloalkyl, aryl and aromatic acyl), hydroxy, alkoxy (i.e. alkyl-oxy), carboxy, oxo (forming a keto or aldehyde functionality), alkoxycarbonyl, alkylcarbonyl, formyl, aryl, aryloxycarbonyl, aryloxy, arylamino, arylcarbonyl, amino, mono- and dialkylamino, carbamoyl, mono- and dialkyl-aminocarbonyl, alkylcarbonylamino, cyano, alkanoyloxy, nitro, alkylthio and halogen (F, Cl, Br, I).

The "protecting group that is removable by catalytic hydrogenation" refers to groups whose C—O bond is cleaved by addition of hydrogen in the presence of catalytic amounts of palladium, Raney nickel or another appropriate metal catalyst known for use in hydrogenolysis, resulting in the regeneration of the OH group. Such protecting groups are well known to the skilled man and are thoroughly discussed [7]. Suitable protecting groups include benzyl, diphenylmethyl(benzhydryl), 1-naphthylmethyl, 2-naphthylmethyl or triphenylmethyl (trityl) groups, each of which may be optionally substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen. Preferably, such substitution, if present, is on the aromatic ring(s). Particularly preferred protecting groups are benzyl or 1-naphthylmethyl groups, both are optionally substituted with one or more groups selected from phenyl, alkyl or halogen. More preferably, the protecting group is selected from unsubstituted benzyl, unsubstituted 1-naphthylmethyl, 4-chlorobenzyl and 4-methylbenzyl. These particularly preferred and more preferable protecting groups have the advantage that the by-products of the hydrogenolysis are exclusively toluene, 1-methylnaphthalene, or substituted toluene or 1-methyl-naphthalene derivatives. Such by-products can easily be removed even in multi ton scales from water soluble oligosaccharide products via evaporation and/or extraction processes.

First aspect of the present application relates to a method for the preparation of 6'-O-sialyllactose or a salt thereof, comprising the steps of:

a) reaction of an acceptor of general formula 3

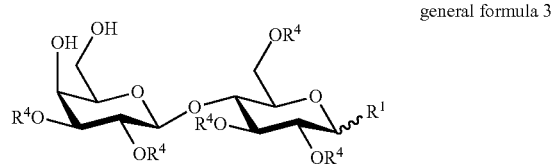

general formula 3 wherein R¹ is —OR², which R² is a group removable by catalytic hydrogenation, or R¹ is —SR³, which R³ is selected from optionally substituted alkyl, optionally substituted aryl and optionally substituted benzyl, or R¹ is —NH—C(R")=C(R')₂, wherein each R' independently of each other is an electron withdrawing group selected from —CN, —COOH, —COO-alkyl, —CO-alkyl, —CONH₂, —CONH-alkyl and —CON(alkyl)₂, or wherein the two R'-groups is linked together and represent —CO—(CH₂)₂₋₄—CO— and thus form with the carbon atom to which they are attached a 5-7 membered cycloalkan-1,3-dion, in which dion any of the methylene groups is optionally substituted with 1 or 2 alkyl groups, and R" is H or alkyl, R⁴ is selected from optionally substituted acyl and benzyl substituted by 1-3 methoxy group(s), with a donor of general formula 4

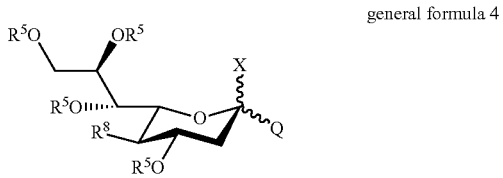

general formula 4 wherein R⁵ is optionally substituted acyl,
R⁸ is selected from —NHAc and —NAc₂,
Q is COO-alkyl, which alkyl is optionally substituted, and
X is leaving group, to yield a compound of general formula 2

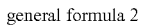
general formula 2

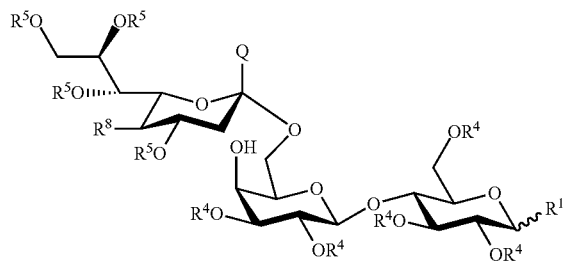

wherein $R^1$, $R^4$, $R^5$, $R^8$ and Q are as defined above,
b) deprotection of a compound of general formula 2 to give a compound of general formula 1 or salts thereof

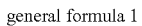
general formula 1

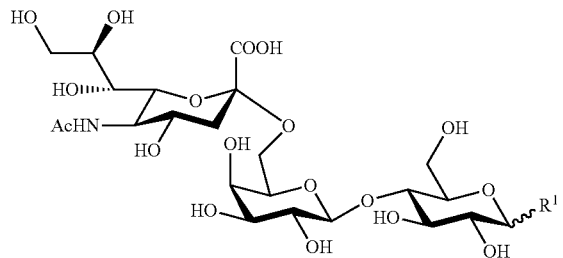

wherein $R^1$ is as defined above, and
c) subsequently converting the compound of general formula 1 or salts thereof into 6'-O-sialyllactose or salts thereof.

With regard to step c) of the first aspect compounds of general formula 1 or salts thereof are treated to deprotect them anomerically thus 6'-O-sialyllactose or salts thereof can be obtained. Particularly, 6'-SL or salts thereof can be produced by subjecting a compound of general formula 1 or salts thereof i) to catalytic reduction when $R^1$ is —$OR^2$, wherein $R^2$ is a group removable by catalytic hydrogenation, ii) to activation with a thiophilic reagent followed by hydrolysis when $R^1$ is —$SR^3$, wherein $R^3$ is selected from optionally substituted alkyl, optionally substituted aryl and optionally substituted benzyl, iii) to treatment with an amine or halogen followed by hydrolysis at neutral or mild acidic pH when $R^1$ is —NH—C(R")=C(R')$_2$, wherein each R' is an electron withdrawing group selected from —CN, —COOH, —COO-alkyl, —CO-alkyl, —CONH$_2$, —CONH-alkyl and —CON(alkyl)$_2$, or wherein the two R'-groups is linked together and represent —CO—(CH$_2$)$_{2-4}$—CO— and thus form with the carbon atom to which they are attached a 5-7 membered cycloalkan-1,3-dion, in which dion any of the methylene groups is optionally substituted with 1-2 alkyl groups, and R" is H or alkyl.

In one embodiment $R^1$ represents —$OR^2$, wherein $R^2$ is a group removable by catalytic hydrogenation, that is optionally substituted benzyl, diphenylmethyl(benzhydryl), 1-naphthylmethyl, 2-naphthylmethyl or triphenylmethyl (trityl) groups, whose removal typically takes place in a protic solvent or in a mixture of protic solvents. A protic solvent may be selected from a group consisting of water, acetic acid or $C_1$-$C_6$ alcohol. Mixture of one or more protic solvents with one or more proper aprotic organic solvents miscible partially or fully with the protic solvent(s) (such as THF, dioxane, ethyl acetate, acetone, etc.) may also be applied. Water, one or more $C_1$-$C_6$ alcohols or a mixture of water and one or more $C_1$-$C_6$ alcohols are preferably used as solvent system. Solutions containing the carbohydrate derivatives in any concentration or suspensions of the carbohydrate derivatives with the solvent(s) used are also applicable. The reaction mixture is stirred at 10-100° C. temperature range, preferably between 20-60° C. in hydrogen atmosphere of 1-50 bar in the presence of a catalyst such as palladium, Raney nickel or any other appropriate metal catalyst, preferably palladium on charcoal or palladium black, until reaching the completion of the reaction. Catalyst metal concentrations generally range from 0.1% to 10% based on the weight of carbohydrate. Preferably, the catalyst concentrations range from 0.15% to 5%, more preferably 0.25% to 2.25%. Transfer hydrogenation may also be performed, when the hydrogen is generated in situ from cyclohexene, cyclohexadiene, formic acid or ammonium formate. Addition of organic or inorganic bases/acids and/or basic and/or acidic ion exchange resins can also be used to improve the kinetics of the hydrogenolysis. The use of basic substances is especially preferred when halogen substituents are present on the substituted benzyl moieties of the precursors. Preferred organic bases are including but not limited to triethylamine, diisopropyl ethylamine, ammonia, ammonium carbamate, diethylamine, etc. Preferred organic/inorganic acids are including but not limited to formic acid, acetic acid, propionic acid, chloroacetic acid, dichloroacetic acid, trifluoroacetic acid, HCl, HBr, etc. The conditions proposed above allow simple, convenient and delicate removal of the solvent(s) giving rise to pure 6'-SL. 6'-SL and salts thereof can be isolated from the reaction mixture using conventional work-up procedures in crystalline, amorphous solid, syrupy form or concentrated aqueous solution.

In another embodiment of producing 6'-O-sialyllactose or salts $R^1$ is —$SR^3$ and $R^3$ is optionally substituted alkyl, optionally substituted aryl or optionally substituted benzyl in general formula 1. Thioglycosides typically act as donor in glycosidation reactions, thus conducting a glycosidation reaction in the presence of water results in the formation of the corresponding reducing sugar. In a typical glycosylation a thioglycoside according to general formula 1 is dissolved in water or dipolar aprotic solvents containing water followed by addition of a thiophilic activator such as mercury(II) salts, Br$_2$, I$_2$, NBS, NIS, triflic acid or triflate salts, or mixtures thereof. The activated intermediate reacts easily with water being present in the reaction milieu and 6'-O-sialyllactose or salts thereof are produced.

In another embodiment 6'-O-sialyllactose and salts thereof can be formed by removal of acyclic vinylogous amine group of compounds of general formula 1, wherein $R^1$ is —NH—C(R")=C(R')$_2$, and R' is electron withdrawing groups selected from —CN, —COOH, —COO-alkyl, —CO-alkyl, —CONH$_2$, —CONH-alkyl, —CONH-benzyl, —CON(alkyl)$_2$ and —CON(benzyl)$_2$, or two R'-groups linked together represent —CO—(CH$_2$)$_{2-4}$—CO— and thus form with the adjacent carbon atom an 5-7 membered cycloalkan-1,3-dion and any of the methylene groups may be substituted with 1 or 2 alkyl groups, and R" represents H or alkyl. The enamine structure can be split by treatment with amino compounds or halogen. Solvents used for the reaction are including but not limited to methanol, ethanol, water, acetic acid, ethyl acetate, etc., and mixtures thereof can be also applied. Amino compounds used for transamination are typically aqueous or anhydrous primary amines, like ethylamine, propylamine, butylamine etc.; hydrazines, like hydrazine hydrate, hydrazine acetate etc.; hydroxylamine derivatives; aqueous ammonia solution or ammonia gas in anhydrous conditions. The acyclic vinylogous amine can also be cleaved by using halogen such as chlorine gas or bromine. Both types of reaction yield amine functionality at the anomeric position whose hydrolysis under neutral or slightly acidic pH (pH≈4-7) readily provides 6'-O-sialyllactose.

If 6'-O-sialyllactose is obtained in the abovementioned reactions, it is converted to a salt thereof, and if desired, a salt of 6'-O-sialyllactose is converted to another salt of 6'-O-sialyllactose.

In a preferred embodiment $R^1$ in a compound of general formula 1 is —$OR^2$, which $R^2$ is a group removable by catalytic hydrogenation, preferably selected from benzyl, 4-methylbenzyl, 4-chlorobenzyl and 1-naphthylmethyl.

With regard to step b) of the first aspect of the present application in compounds according to general formula 2 all of the functional groups are protected expect for 4'-OH, which protective groups are frequently used in carbohydrate chemistry. The protecting groups can be removed either successively giving rise to partially protected trisaccharides (vide infra) and at last compounds of general formula 1 or salts thereof or in one step leading to directly compounds of general formula 1 or salts thereof. All combination of deprotection steps as used herein can be performed in any order, thus selecting the proper conditions needed to remove them as well as conducting deprotection steps in succession fall under the skilled person's competence.

According to one embodiment in step b) of the first aspect compounds of general formula 1 or salts thereof can be obtained from a group of compounds of general formula 2 characterized by general formula 2A general formula 2A

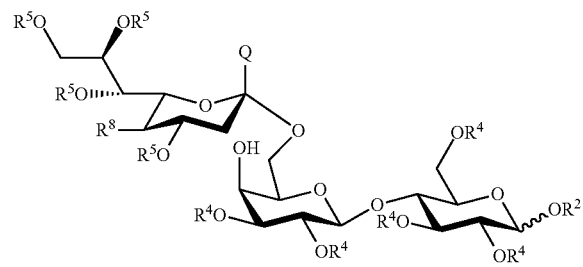

wherein $R^2$ is a group removable by catalytic hydrogenation,
$R^4$ and $R^5$ are independently from each other optionally substituted acyl,
$R^8$ is selected from —NHAc or —$NAc_2$ and
Q is —COO-alkyl, which alkyl is optionally substituted, comprising the following steps:
a) base catalyzed transesterification reaction followed by a basic hydrolysis, optional acidification and optional salt formation, or
b) basic hydrolysis, optional acidification and optional salt formation.

The term "base catalyzed transesterification deprotection" means a reaction, where the acyl protective groups from hydroxyls are removed in an alcohol solvent such as methanol, ethanol, propanol, t-butanol, etc. in the presence of an alcoholate like NaOMe, NaOEt, KO$^t$Bu, etc. at 20-100° C. temperatures. The alcohol and the alcoholate should be matched. The use of co-solvent as toluene or xylene might be beneficial in order to control particle size of the product and to avoid gel formations. Under this condition only O-acyls can be readily deprotected and when $R^8$ is —$NAc_2$ one of the acetyl is also removed. The Q group may be transesterified. In a preferred embodiment catalytic amount of NaOMe is used in methanol (Zemplén de-O-acylation). The term "basic hydrolysis" generally means base catalyzed hydrolysis in water, alcohol or water-organic solvent mixtures, in homogeneous or heterogeneous reaction conditions at temperatures varying from 0-100° C. The base of choice is generally a strong base, e.g. LiOH, NaOH, KOH, Ba(OH)$_2$, $K_2CO_3$, basic ion exchange resins, tetraalkylammonium hydroxides, etc. The bases can be used in the form of an aqueous solution as well. This condition affects O-acyls, when Q is ester it is also hydrolyzed and when $R^8$ is —$NAc_2$ one of the acetyl is also removed. In a preferred embodiment the base is NaOH and the solvent is methanol.

"Optional acidification" intends to mean that an acidification step can be performed when the acid form of compounds of general formula 1 is needed after base catalyzed transesterification deprotection or basic hydrolysis.

"Optional salt formation" means that a compound of general formula 1 in acidic form, if needed, is converted into its salt different to that formed after base catalyzed transesterification deprotection or basic hydrolysis. A salt of a compound of general formula 1 means an associated ion pair consists of the negatively charged acid residue of compound of general formula 1 and a cation in any stoichiometric proportion. Cations, as used in the present context, can be atoms or molecules with positive charge. The cation may be inorganic as well as organic cation. Preferred inorganic cations are ammonium ion, alkali metal, alkali earth metal and transition metal ions, more preferably Na$^+$, K$^+$, Ca$^{2+}$, Mg$^{2+}$, Ba$^{2+}$, Fe$^{2+}$, Zn$^{2+}$, Mn$^{2+}$ and Cu$^{2+}$, most preferably K$^+$, Ca$^{2+}$, Mg$^{2+}$, Ba$^{2+}$, Fe$^{2+}$ and Zn$^{2+}$. Basic organic compounds in positively charged form may be relevant organic cations. Such preferred positively charged organic molecules are diethyl amine, triethyl amine, diisopropyl ethyl amine, ethanolamine, diethanolamine, triethanolamine, imidazol, piperidine, piperazine, morpholin, benzyl amine, ethylene diamine, meglumin, pyrrolidine, choline, tris-(hydroxymethyl)-methyl amine, N-(2-hydroxyethyl)-pyrrolidine, N-(2-hydroxyethyl)-piperidine, N-(2-hydroxyethyl)-piperazine, N-(2-hydroxyethyl)-morpholine, L-arginine, L-lysine, oligopeptides having L-arginine or L-lysine unit or oligopeptides having free amino group on N-terminal, etc., all in protonated form. An inorganic and organic salt of compound of general formula 1 can be obtained from a compound of general formula 1 in acidic form. The pH of the solution of the free acid in alcohol or alcohol/water is adjusted to 8, 5-11 with a base; if the base is an inorganic one, it can be selected from alkali metal, alkali earth metal and transition metal hydroxides, carbonates and bicarbonates. The mixture is then diluted with alcohol and concentrated in vacuo. The slurry obtained is then filtered and washed with alcohol.

In a preferred realization compounds of general formula 2A, wherein $R^2$ is selected from benzyl, 4-methylbenzyl, 4-chlorobenzyl and 1-naphthylmethyl, $R^4$ is selected from isobutyryl, pivaloyl and optionally substituted benzoyl, preferably pivaloyl and benzoyl, $R^5$ is acetyl, Q is —$COOCH_3$ and —$OR^2$ is in (3 are deprotected.

According to another embodiment in step b) of the first aspect compounds of general formula 2B belonging to compounds of general formula 2

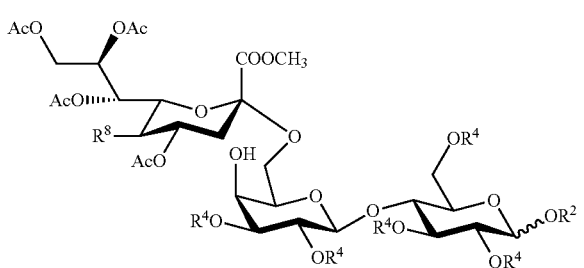

general formula 2B wherein $R^2$ is a group removable by catalytic hydrogenation,
$R^4$ is optionally substituted acyl provided that acetyl is excluded, and
$R^8$ is selected from —NHAc and —NAc$_2$,
are subjected to selective acidic deprotection to give compounds of general formula 2C

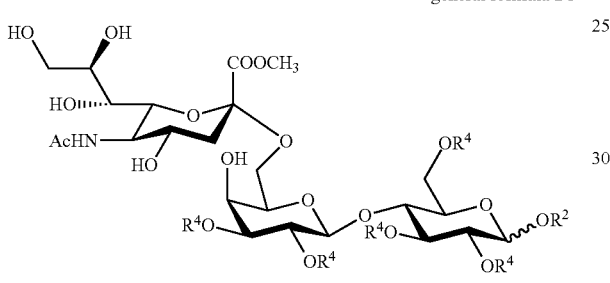

general formula 2C wherein $R^2$ and $R^4$ are as defined above,
followed by
a) base catalyzed transesterification reaction followed by basic hydrolysis, optional acidification and optional salt formation, or
b) basic hydrolysis, optional acidification and optional salt formation
to give a compound of general formula 1 or salts thereof.

Compounds of general formula 2C can be obtained in a delicate way from compounds of compounds 2B. The present inventors recognized that the acetyl groups in the sialic acid residue ($R^5$ is acetyl) can be selectively removed when the lactose portion is protected by acyls different form acetyl ($R^4$ is optionally substituted acyl provided that acetyl is excluded) due to the higher reactivity of acetyls towards acidic transesterification than other acyls. The deprotection step can be carried out in a $C_{1-6}$ alcohol or mixture of $C_{1-6}$ alcohols, preferably methanol and ethanol in the presence of an acid, generally a protic acid selected from but not limited to acetic acid, trifluoroacetic acid, HCl, formic acid, sulphuric acid, perchloric acid, oxalic acid, p-toluenesulfonic acid, benzenesulfonic acid, cation exchange resins, etc., preferably strong inorganic acid which may be present in from catalytic amount to excess. The hydrolysis may be conducted at temperatures between 0 and 20° C., preferably at 5-10° C. until TLC shows complete or nearly complete reaction which takes from about 2 hours to 3 days depending on temperature, concentration and pH.

In a preferred embodiment —OR$^2$ is in β, $R^2$ is benzyl, 4-methylbenzyl, 4-chlorobenzyl and 1-naphthylmethyl, $R^4$ is selected from isobutyryl, pivaloyl and optionally substituted benzoyl, preferably benzoyl and the acid catalyst of the selective acidic deprotection is sulphuric acid. According to another realization in step b) of the first aspect a group of compounds of general formula 2 characterized by general formula 2D

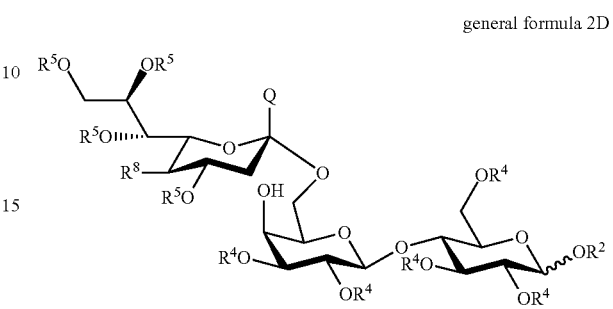

general formula 2D wherein $R^2$ is a group removable by catalytic hydrogenation,
$R^4$ is benzyl substituted by 1-3 methoxy group(s),
$R^5$ is optionally substituted acyl,
$R^8$ is selected from —NHAc or —NAc$_2$ and
Q is —COO-alkyl, which alkyl is optionally substituted
is deprotected comprising the steps of:
a) base catalyzed transesterification reaction resulting in another compounds of general formula 2D, wherein $R^2$ is as defined above, $R^4$ is benzyl substituted by 1-3 methoxy group(s), $R^5$ is H, $R^8$ is —NHAc and Q is —COO-alkyl, which alkyl is optionally substituted, followed by
  aa) dichlorodicyanoquinone (DDQ) or cerium(IV) ammonium nitrate (CAN) mediated oxidation resulting in another compound of general formula 2D, wherein $R^2$ is as defined above, each of $R^4$ and $R^5$ are H, $R^8$ is —NHAc and Q is —COO-alkyl, which alkyl is optionally substituted, followed by basic hydrolysis, optional acidification and optional salt formation, or
  ab) basic hydrolysis, optional acidification and optional salt formation resulting in another compound of general formula 2D, wherein $R^2$ is as defined above, $R^4$ is benzyl substituted by 1-3 methoxy group(s), $R^5$ is H, $R^8$ is —NHAc and Q is —COOH in either protonated or deprotonated form, followed dichlorodicyanoquinone (DDQ) or cerium(IV) ammonium nitrate (CAN) mediated oxidation
to give a compound of general formula 1 or salts thereof, or
b) dichlorodicyanoquinone (DDQ) or cerium(IV) ammonium nitrate (CAN) mediated oxidation resulting in another compound of general formula 2D, wherein $R^2$ is above, $R^4$ is H, $R^5$ is optionally substituted acyl, $R^8$ is selected from —NHAc and —NAc$_2$ and Q is —COO-alkyl, which alkyl is optionally substituted, followed by
  ba) base catalyzed transesterification reaction followed by basic hydrolysis, optional acidification and optional salt formation, or
  bb) basic hydrolysis, optional acidification and optional salt formation
to give a compound of general formula 1 or salts thereof, or
c) basic hydrolysis, optional acidification and optional salt formation resulting in another compound of general formula 2D, wherein $R^2$ is as defined above, $R^4$ is benzyl substituted by 1-3 methoxy group(s), $R^5$ is H, $R^8$ is —NHAc and Q is —COOH in either protonated or deprotonated form, followed by dichlorodicyanoquinone (DDQ) or cerium(IV) ammonium nitrate (CAN) mediated oxidation to give a compound of general formula 1 or salts thereof.

The term "—COOH in either protonated or deprotonated form" in certain compounds of general formula 2D intends to mean that the carboxylic group in those compounds of general formula 2D is in either acidic (protonated) form thus signifying they are acids or the carboxylic group in those compounds of general formula 2D is in carboxylate (—COO⁻) form signifying they are salts, in which salts the positively charged counter-ion may be an inorganic or organic cation. These inorganic and organic cations are specified above.

The protected 6'-O-sialyllactose may contain 1, 2 or 3 methoxy substituted benzyl groups on the lactose portion, preferably p-methoxybenzyl ($R^4$=PMB). It is well-known that methoxy substituted benzyl ethers are more readily cleaved oxydatively that unsubstituted benzyl ethers, thus a selective deprotection may be possible if the aglycon or Q contains benzyl group. Typical oxidative agents are dichlorodicyanoquinone (DDQ) and cerium(IV) ammonium nitrate (CAN), the reaction runs in organic solvent in the presence of water, preferably in dichloromethane or acetonitrile, resulting in smooth removal of methoxy-benzyl ether protecting group.

With regard to step a) of the first aspect of the present invention a compound of general formula 3 ($R^1$ is —$OR^2$, which $R^2$ is a group removable by catalytic hydrogenation, or $R^1$ is —$SR^3$, which $R^3$ is optionally substituted alkyl, optionally substituted aryl or optionally substituted benzyl, or $R^1$ is —NH—C(R")=C(R')$_2$, wherein each R' independently of each other is an electron withdrawing group selected from —CN, —COOH, —COO-alkyl, —CO-alkyl, —CONH$_2$, —CONH-alkyl and —CON(alkyl)$_2$, or wherein the two R'-groups is linked together and represent —CO—(CH$_2$)$_{2-4}$—CO— and thus form with the carbon atom to which they are attached a 5-7 membered cycloalkan-1,3-dion, in which dion any of the methylene groups is optionally substituted with 1 or 2 alkyl groups, R" is H or alkyl, $R^4$=optionally substituted acyl or benzyl substituted by 1, 2 or 3 methoxy) is reacted with a compound according to general formula 4 ($R^5$=optionally substituted acyl, $R^8$=—NHAc or —NAc$_2$, Q is —COO-alkyl, which alkyl is optionally substituted, X is a leaving group) to obtain compounds of general formula 2 ($R^4$ is optionally substituted acyl or benzyl substituted by 1-3 methoxy group(s), $R^5$ is optionally substituted acyl, $R^8$ is —NHAc or NAc$_2$ and Q is —COO-alkyl, which alkyl is optionally substituted) (Scheme 2.).

Scheme 2.

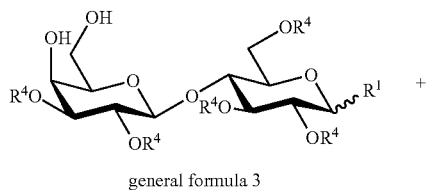

general formula 3

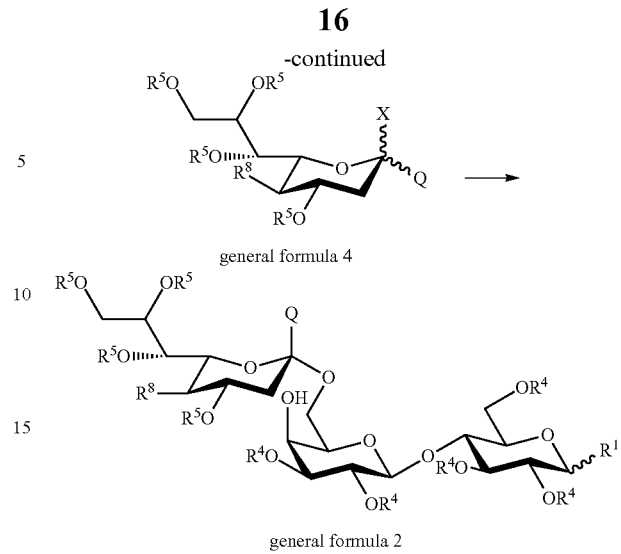

general formula 2

The coupling of the lactose acceptor of general formula 3 with the sialyl donor of general formula 4 can be carried out an aprotic solvent or in a mixture of aprotic solvents in the presence of an activator (promoter or catalyst) so as to lead to the desired glycosylated product. The new interglycosidic linkage is formed by the nucleophilic displacement of the leaving group X of donor according to general formula 4 with the 6'-OH group of acceptor according to general formula 3. Other functional groups in both participating reactants have to be masked with protecting groups. Particular care has to be taken with regard to the stereoselectivity. The stereochemical outcome may be affected by different factors like the presence or absence of a participating group at the ring carbon adjacent to the anomeric centre of the donor, the nature of the leaving group X, solvent effect, nature of the protective groups on both the donor and acceptor, nature of the promoters or catalysts, temperature, pressure, steric interactions between the donor and acceptor, and like. In case of sialic acid derivatives an array of anomeric activation for glycosylation is developed and available to a skilled person engaged in sialic acid chemistry. These methodologies are expansively discussed by reviews [6]. For the sake of examples some general considerations are briefly mentioned below depending on the X-group.

The glycosyl halides (X means F, Cl, Br, I) are frequently used in glycosylation reaction because of their easy accessibility and satisfactory reactivity. Typically, anomeric halides follow the reactivity order F<Cl<Br<I for nucleophilic displacement. The glycosylation reactions are generally promoted by heavy metal ion, mainly mercury or silver, and Lewis acids.

Glycosyl trichloroacetimidates (X=—OC(=NH)CCl$_3$) can be easily prepared by the addition of the free anomeric OH to trichloroacetonitrile under inorganic or organic base catalysis. In a typical glycosidation reaction catalytic amount of Lewis acid, such as trimethylsilyl triflate or BF$_3$-etherate, promotes the coupling.

Thioglycosides (X denotes alkylthio- or phenylthio-group) can be activated by thiofilic promoters such as mercury(II) salts, Br$_2$, I$_2$, NBS, NIS, triflic acid, triflate salts, BF$_3$-etherate, trimethylsilyl triflate, dimethyl-methylthio sulphonium triflate, phenylselenyl triflate, iodonium dicollidine perchlorate, tetrabutylammonium iodide or mixtures thereof, in condensation reactions, preferably by Br$_2$, NBS or NIS.

Glycosyl phosphite donors (X is —O—P—(O-[alkyl or benzyl])$_2$), can be promoted with NBS, NIS, TMSOTf, TfOH, Tf$_2$O, ZnCl$_2$, BF$_3$.OEt$_2$, LiClO$_4$, DTBPI, Bu$_4$NI, AgClO$_4$, LiClO$_4$, Sn(OTf)$_2$ or mixtures thereof, preferably TMSOTf.

Glycosyl acetates (X represents —OAc) in glycosylation reaction are first subjected to electrophilic activation providing a reactive intermediate, then treated with the nucleophilic OH-acceptor. Typical activators of choice are Bronsted acids (such as TsOH, HClO$_4$, sulfamic acid), Lewis acids (such as ZnCl$_2$, SnCl$_4$, triflate salts, BF$_3$-etherate, trityl perchlorate, AlCl$_3$, triflic anhydride) and their mixtures.

According to a preferred method a group of compounds of general formula 4, which is characterized by general formula 4A

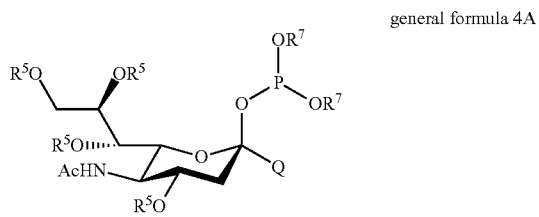

general formula 4A wherein R$^5$ is optionally substituted acyl, Q is —COO-alkyl, which alkyl is optionally substituted and R$^7$ is substituted benzyl, are employed in the coupling reactions. The reaction runs in aprotic solvent, preferably in dichloromethane, THF, toluene, acetonitrile or in mixtures thereof, more preferably in dichloromethane/acetonitrile mixture, at temperatures between −78-0° C., in the presence of promoter like NBS, NIS, TMSOTf, TfOH, Tf$_2$O, ZnCl$_2$, BF$_3$.OEt$_2$, LiClO$_4$, DTBPI, Bu$_4$NI, AgClO$_4$, LiClO$_4$, Sn(OTf)$_2$ or mixtures thereof, preferably TMSOTf.

In a preferred embodiment the donor and acceptor are dissolved in the solvent mixture of THF/DCM in ratios 1:1 to 1:5 and temperature is kept between −40° C. to −10° C. A promoter of choice including but limited to TMSOTf, TfOH, BF$_3$.Et$_2$O, DTPI, tetrabutylammonium iodide, etc. is added and the reaction is stirred until it reaches completion.

In another preferred embodiment the donor and acceptor are dissolved in the solvent mixture of CH$_3$CN/DCM in ratios 1:1.7 to 1:5 and temperature is kept between −40° C. to −30° C. A promoter of choice is added including but limited to TMSOTf, TfOH, BF$_3$.Et$_2$O, DTPI, tetrabutylammonium iodide, etc. and the reaction is stirred till it reaches completion.

In another preferred embodiment the donor and acceptor are dissolved in the solvent mixture of Tol/CH$_3$CN/DCM preferably in a ratio 1:1:1 and temperature is kept between −40° C. to −20° C. A promoter of choice is added including but limited to TMSOTf, TfOH, BF$_3$.Et$_2$O, DTPI, tetrabutylammonium iodide, etc. and the reaction is stirred till it reaches completion.

In a preferred donor of general formula 4A R$^5$ is acetyl, R$^7$ is 4-chlorobenzyl or 4-bromobenzyl, and Q is —COOMe.

With regard to the production of compounds of general formula 2 starting from acceptor of general formula 3 and donor of general formula 4, another preferred realization comprises the use of another group of compounds of general formula 4, which is characterized under general formula 4B

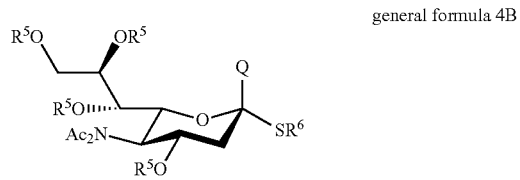

general formula 4B wherein R$^5$ is optionally substituted acyl, Q is —COO-alkyl, which alkyl is optionally substituted and R$^6$ is selected form C$_{2-6}$ alkyl, C$_{3-6}$ cycloalkyl and optionally substituted benzyl. The glycosylation is carried out in aprotic solvent(s) like chloroform, dichloromethane, toluene, dioxane, THF, acetonitrile or mixture thereof, preferably chloroform or dichloromethane, under the activation of NIS, NBS, Br$_2$, triflic acid, silver triflate, BF$_3$-etherate or mixture thereof.

In a preferred donor of general formula 4B R$^5$ is acetyl, R$^6$ is selected from ethyl, isopropyl, t-butyl, benzyl and cyclohexyl, and Q is —COOMe.

A further preferred embodiment relates to the use of compounds of general formula 4C in the sialylation reaction

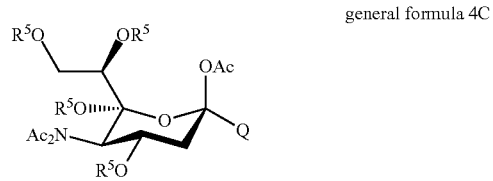

general formula 4C wherein R$^5$ is optionally substituted acyl, and Q is —COO-alkyl, which alkyl is optionally substituted. The glycosylation is carried out in aprotic solvent(s) like chloroform, dichloromethane, toluene, dioxane, THF, acetonitrile or mixture thereof, preferably chloroform or dichloromethane, under the activation of Bronsted or Lewis acid. A compound of general formula 4C wherein R$^5$ is acetyl and Q is —COOMe is the preferred donor of choice.

In a preferred donor of general formula 4C R$^5$ is acetyl, and Q is —COOMe.

In another embodiment the synthesis of compounds according to general formula 2 comprises the use of compounds of the general formula 3A

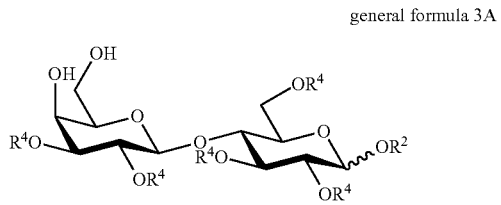

general formula 3A wherein R$^2$ is a group removable by catalytic hydrogenation, and R$^4$ is selected from benzyl substituted by 1-3 methoxy group(s) and optionally substituted acyl provided that acetyl is excluded.

In a preferred embodiment —OR$^2$ is in β, R$^2$ is selected from benzyl, 4-methylbenzyl, 4-chlorobenzyl and 1-naphthylmethyl, and R$^4$ is selected from isobutyryl, pivaloyl and benzoyl. 6'-O—Sialyllactose and several 6'-O-sialyllactose intermediates in acidic form have limited chemical stability in aqueous solution due to the high acidity of the sialic acid structural motif and to the low hydrolytic stability of the α-O-sialyl linkage. For example, 6'-O-sialyllactose decomposes in aqueous solution at room temperature into sialic acid and lactose by autocatalysis. The low acid stability of sialyllactose itself in aqueous solutions is the major obstacle of isolation, and of enzymatic or chemical technologies targeting the preparation of 6'-O-sialyllactose. Furthermore, 6'-O-sialyllactose is not crystalline preventing the development of efficient purification methodologies required for the preparation of high quality 6'-O-sialyllactose product.

The present invention comprises providing new salts of 6'-O-sialyllactose. The term "salt of 6'-O-sialyllactose" means an associated ion pair consists of the negatively charged acid residue of 6'-O-sialyllactose and a cation in any stoichiometric proportion. Cations, as used in the present context are atoms or molecules with positive charge. The cation may be inorganic as well as organic cation. Preferred inorganic cations are ammonium ion, alkali metal, alkali earth metal and transition metal ions, more preferably $Na^+$, $K^+$, $Ca^{2+}$, $Mg^{2+}$, $Ba^{2+}$, $Fe^{2+}$, $Zn^{2+}$, $Mn^{2+}$ and $Cu^{2+}$, most preferably $K^+$, $Ca^{2+}$, $Mg^{2+}$, $Ba^{2+}$, $Fe^{2+}$ and $Zn^{2+}$. Basic organic compounds in positively charged form may be relevant organic cations. Such preferred positively charged counterparts are diethyl amine, triethyl amine, diisopropyl ethyl amine, ethanolamine, diethanolamine, triethanolamine, imidazol, piperidine, piperazine, morpholin, benzyl amine, ethylene diamine, meglumin, pyrrolidine, choline, tris-(hydroxymethyl)-methyl amine, N-(2-hydroxyethyl)-pyrrolidine, N-(2-hydroxyethyl)-piperidine, N-(2-hydroxyethyl)-piperazine, N-(2-hydroxyethyl)-morpholine, L-arginine, L-lysine, oligopeptides having L-arginine or L-lysine unit or oligopeptides having free amino group on N-terminal, etc., all in protonated form. Such salt formations can be used to modify characteristics of the complex molecule as a whole, such as stability, compatibility to excipients, solubility and ability to form crystals.

Thus it is provided the $Zn^{2+}$ salt of 6'-O-sialyllactose as novel inorganic 6'-SL salt:

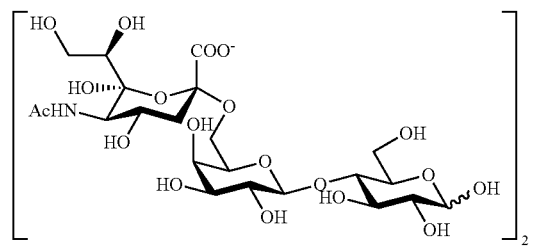

In addition the present application relates to providing 6'-SL organic salts of formula I

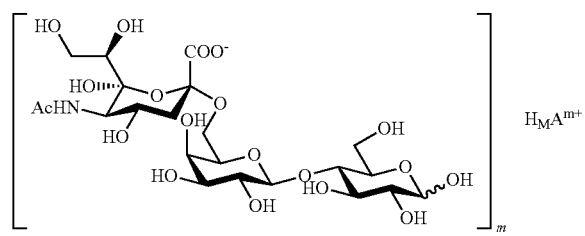

formula I wherein A means any organic base and m is an integer number.

Compound A as organic base comprises preferably amine-type bases like diethyl amine, triethyl amine, diisopropyl ethyl amine, ethanolamine, diethanolamine, triethanolamine, imidazol, piperidine, piperazine, morpholine, benzyl amine, ethylene diamine, meglumin, pyrrolidine, choline, tris-(hydroxymethyl)-methyl amine, N-(2-hydroxyethyl)-pyrrolidine, N-(2-hydroxyethyl)-piperidine, N-(2-hydroxyethyl)-piperazine, N-(2-hydroxyethyl)-morpholine, L-arginine, L-lysine, oligopeptides having L-arginine or L-lysine unit or oligopeptides having free amino group on N-terminal, etc. These bases are in protonated form when associated with 6'-SL. The especially preferred organic amines are selected from diethyl amine, tris-(hydroxymethyl)-methyl amine, ethanolamine and choline.

Inorganic and organic salts of 6'-SL can be obtained from acidic 6'-SL. The pH of the solution of the free acid in alcohol or alcohol/water is adjusted to 8, 5-11 with the selected base; if the base is an inorganic one it can be chosen from metal hydroxides, carbonates and bicarbonates. The mixture is then diluted with alcohol and concentrated in vacuo. The slurry obtained is then filtered and washed with alcohol.

In an alternative way an inorganic or organic salt a compounds of general formula 1 wherein $R^1$ is $—OR^2$, which $R^2$ is a group removable by catalytic hydrogenation (see above) is subjected to catalytic hydrogenolysis to give rise to the corresponding inorganic or organic salt of 6'-SL.

It is strongly emphasised that the novel 6'-O-sialyllactose salts may be crystalline, they can be considered as sole chemical entities such as α- or β-anomers or even an anomeric mixture thereof. They might exist in anhydrous, hydrated as well as solvated forms. In addition, the novel 6'-SL salts can be isolated as amorphous solid, syrup or concentrated aqueous solution as well.

6'-O-Sialyllactose and sialylated human milk oligosaccharides are of great importance which is directly linked to their unique biological activities such as antibacterial, antiviral, immune system and cognitive development enhancing activities. Sialylated human milk oligosaccharides including 6'-SL, optionally in combination with other sialic acid and/or N-acetyllactosamine and/or fucose containing human milk oligosaccharides, are found to act as prebiotics in the human intestinal system helping to develop and maintain the intestinal flora. Furthermore they have also proved to be anti-inflammatory, and therefore these compounds are attractive components in the nutritional industry for the production of, for example, infant formulas, infant cereals, clinical infant nutritional products, toddler formulas, or as dietary supplements or health functional food for children, adults, elderly or lactating women, both as synthetically composed and naturally occurring compounds and salts thereof. Thus 6'-SL $Zn^{2+}$ salt and/or 6'-SL organic salts according to the present invention are suitable for pharmaceutical and nutritional use.

In another aspect, the present invention provides pharmaceutical composition comprising 6'-SL $Zn^{2+}$ salt and/or 6'-SL organic salts as active ingredient and one or more pharmaceutically acceptable carriers including but not limited to additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.). Suitable carriers are described in the most recent edition of Remington's Pharmaceutical Sciences, a standard reference text in the field. The dosage form for administration includes, for example, tablets, powders, granules, pills, suspensions, emulsions, infusions, capsules, syrups, injections, liquids, elixirs, extracts and tincture.

In a further embodiment 6'-SL $Zn^2$ salt and/or 6'-SL organic salts according to the present invention are used for the preparation of pharmaceutical compositions. Pharmaceutical compositions can be manufacture by means of any usual manner known in the art, e.g. described in the most recent edition of Remington's Pharmaceutical Sciences, a standard reference text in the field.

In a further embodiment it is provided nutritional formulations comprising one or more 6'-SL salts selected form 6'-SL $Zn^2$ salt and/or 6'-SL organic salts according to the present invention such as foods, drinks or feeds. The nutritional formulation may contain edible micronutrients, vitamins and minerals as well. The amounts of such ingredient may vary depending on whether the formulation is intended for use with normal, healthy infants, children, adults or subjects having specialized needs (e.g. suffering from metabolic disorders). Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolized cornstarch, etc.) and proteins from casein, soy-bean, whey or skim milk, or hydrolysates of these proteins, but protein from other source (either intact or hydrolysed) may be used as well. Vitamins may be chosen from the group consisting of vitamin A, B1, B2, B5, B6, B12, C, D, E, H, K, folic acid, inositol and nicotinic acid. The nutritional formula may contain the following minerals and trace elements: Ca, P, K, Na, Cl, Mg, Mn, Fe, Cu, Zn, Se, Cr or I.

In a preferred embodiment the nutritional formulation is an infant formula. Infant formula means a foodstuff intended for particular nutritional use by infants during the first 4-6 months of life and satisfying by itself the nutritional requirements of infants. It may contain one or more probiotic *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil. safflower oil) and vitamins and minerals essential in a daily diet. The infant formula may contain 6'-SL $Zn^{2+}$ salt and/or 6'-SL organic salts according to the present invention in a total amount of 0.1-3.0 g/100 g formula.

In another preferred embodiment the nutritional formulation may be a food supplement including 6'-SL $Zn^{2+}$ salt and/or 6'-SL organic salts according to the present invention. The food supplement may comprise one or more probiotics in an amount sufficient to achieve the desired effect in an individual, preferably in children and adults. The food supplement may also contain vitamins, minerals, trace elements and other micronutritients as well. The food supplement may be for example in the form of tablets, capsules, pastilles or a liquid. The supplement may contain conventional additives selected from but not limited to binders, coatings, emulsifiers, solubilising agents, encapsulating agents, film forming agents, adsorbents, carriers, fillers, dispersing agents, wetting agents, jellifying agents, gel forming agents, etc. The daily dose of 6'-SL $Zn^{2+}$ salt and/or 6'-SL organic salts ranges from 0.1 to 3.0 g.

According to a more preferred embodiment the food supplement is digestive health functional food as the administration of 6'-SL $Zn^{2+}$ salt and/or 6'-SL organic salts provides a beneficial effect on digestive health. Digestive health functional food is a processed food used with intention enhance and preserve digestive health by 6'-SL $Zn^{2+}$ salt and/or 6'-SL organic salts according to the present invention as physiologically functional ingredient or component in forms of tablet, capsule, powder, etc. Different terms such as dietary supplement, nutraceutical, designed food, health product may also be used to refer to functional food.

In a further embodiment 6'-SL $Zn^{2+}$ salt and/or 6'-SL organic salts according to the present invention are used for the preparation of nutritional formulation including foods, drinks and feeds, preferably infant formulas, food supplements and digestive health functional food. The nutritional formulation may be prepared in any usual manner.

Compounds of general formula 1, 2, 3 and 4 are believed to be valuable synthetic intermediates towards 6'-SL. The present inventors surprisingly recognized some of the compounds of general formula 1, 2, 3 and 4 can be obtained in crystalline form. Crystallization or recrystallization is one of the simplest and cheapest methods to isolate a product from a reaction mixture, separate it from contaminations and obtain pure substance. Isolation or purification that uses crystallization makes the whole technological process robust and cost-effective, thus it is advantageous and attractive compared to other procedures. The present invention has a great commercial value in large scale production of 6'-SL providing high purity of intermediates, which cannot be achieved by any other known purification methods. Although some other intermediates have not shown the ability to crystallize, they can be prepared in clean, high-yielding and less by-product forming reactions where usual work-up (extraction, evaporation, precipitation, etc.) procedures have been sufficient to obtain high purity products which have been used without further purification in the next step.

Thus it is provided as valuable 6'-SL intermediate a group of compounds of general formula 1 or a salt thereof, namely compounds of general formula 1A

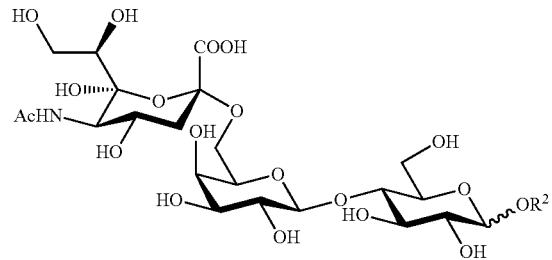

general formula 1A wherein $R^2$ is a group removable by catalytic hydrogenation, preferably benzyl, 4-methylbenzyl, 4-chlorobenzyl and 1-naphthylmethyl and $OR^2$ is in β,
and compounds of general formula 1B

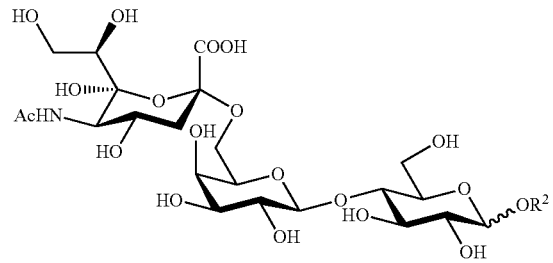

general formula 1B wherein $R^2$ is a group removable by catalytic hydrogenation, in salt form selected from the $Zn^{2+}$, $K^+$, $Ca^{2+}$, $Mg^{2+}$, $Ba^{2+}$, $Fe^{2+}$, $Mn^{2+}$, $Cu^{2+}$ and organic salts.

It is strongly emphasised that novel derivatives characterized by general formulae 1A and 1B can be considered as sole chemical entities such as either α or β anomers, preferably the β anomer, or even an anomeric mixture of α and β isomers. Novel 6'-SL intermediates of general formulae 1A and 1B can be characterized as crystalline solids, oils, syrups, precipitated amorphous material or spray dried products, preferably as crystalline solids. If crystalline, compounds of general formulae 1A and 1B might exist either in anhydrous or in hydrated crystalline forms by incorporating one or several molecules of water into their crystal structures. Similarly, novel compounds characterized by general formulae 1A and 1B might exist as crystalline substances incorporating ligands such as organic molecules and/or ions into their crystal structures.

A compound of general formula 1B as salt means an associated ion pair consists of the negatively charged acid residue of a compound of general formula 1B and a cation in any stoichiometric proportion. The cation may be $K^+$, $Ca^{2+}$, $Mg^{2+}$, $Ba^{2+}$, $Fe^{2+}$, $Zn^{2+}$, $Mn^{2+}$ and $Cu^{2+}$, most preferably $K^+$, $Ca^{2+}$, $Mg^{2+}$, $Ba^{2+}$, $Fe^{2+}$ and $Zn^{2+}$. Basic organic compounds in positively charged form may be relevant organic cations as well. Such preferred positively charged organic molecules are diethyl amine, triethyl amine, diisopropyl ethyl amine, ethanolamine, diethanolamine, triethanolamine, imidazol, piperidine, piperazine, morpholin, benzyl amine, ethylene diamine, meglumin, pyrrolidine, choline, tris-(hydroxymethyl)-methyl amine, N-(2-hydroxyethyl)-pyrrolidine, N-(2-hydroxyethyl)-piperidine, N-(2-hydroxyethyl)-piperazine, N-(2-hydroxyethyl)-morpholine, L-arginine, L-lysine, oligopeptides having L-arginine or L-lysine unit or oligopeptides having free amino group on N-terminal, etc., all in protonated form.

A preferred embodiment relates to compounds of general formula 1B wherein $R^2$ is benzyl, —$OR^2$ is in β and the salt is selected from the $Zn^{2+}$ salt and organic salts, and the organic salt is preferably selected from ethanolammonium, diethyl ammonium, tris-(hydroxymethyl)-methyl ammonium and choline salt.

Novel compounds of general formulae 1A and 1B provided by the present invention can be used for the preparation of 6'-SL itself and other 6'-SL derivatives by using chemical/enzymatic methodologies known in the Art. Novel compounds of general formulae 1A and 1B can also be used as advanced precursors/intermediates for the production/preparation of numerous human milk oligosaccharides. Novel compounds of general formulae 1A and 1B can also be considered as valuable intermediates for the synthesis of complex oligosaccharides/glycoconjugates suitable for therapeutic/nutritional use.

It is provided compounds of general formula 2A

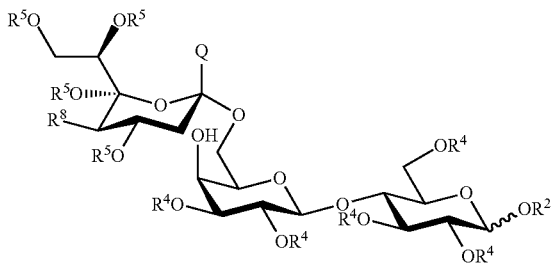

general formula 2A wherein $R^2$ is a group removable by catalytic hydrogenation,
$R^4$ and $R^5$ are independently from each other optionally substituted acyl,
$R^8$ is selected from —NHAc and —NAc$_2$, and
Q is —COO-alkyl, which alkyl is optionally substituted.

It is strongly emphasised that novel derivatives characterized by general formula 2A can be considered as sole chemical entities such as either α or β anomers, preferably the β anomer, or even an anomeric mixture of α and β isomers. Novel 6'-SL intermediates of general formula 2A can be characterized as crystalline solids, oils, syrups, precipitated amorphous material or spray dried products, preferably as crystalline solids. If crystalline, compounds of general formula 2A might exist either in anhydrous or in hydrated crystalline forms by incorporating one or several molecules of water into their crystal structures. Similarly, novel compounds characterized by general formula 2A might exist as crystalline substances incorporating ligands such as organic molecules and/or ions into their crystal structures. Compounds of general formula 2A wherein —$OR^2$ is in β, $R^2$ is selected from benzyl, 4-methylbenzyl, 4-chlorobenzyl and 1-naphthylmethyl, $R^4$ is selected from isobutyryl, pivaloyl and optionally substituted benzoyl, preferably pivaloyl and benzoyl, $R^5$ is acetyl, Q is —$COOCH_3$ are especially preferred.

Novel compounds of general formula 2A provided by the present invention can be used for the preparation of 6'-SL itself and other 6'-SL derivatives by using chemical/enzymatic methodologies known in the Art. Novel compounds of general formulae 2A can also be used as advanced precursors/intermediates for the production/preparation of numerous human milk oligosaccharides. Novel compounds of general formulae 2A can also be considered as valuable intermediates for the synthesis of complex oligosaccharides/glycoconjugates suitable for therapeutic/nutritional use.

Further preferred compounds of general formula 2 are compounds of general formula 2C

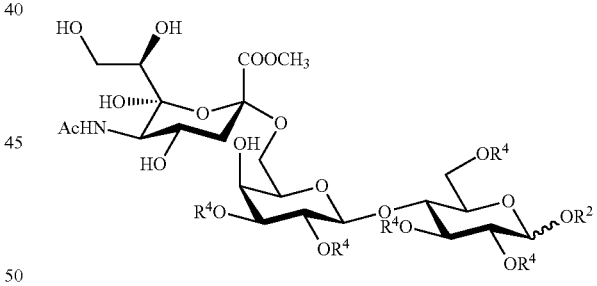

general formula 2C wherein —$OR^2$ is in β, $R^2$ is a group removable by catalytic hydrogenation, preferably benzyl, 4-methylbenzyl, 4-chlorobenzyl and 1-naphthylmethyl, and
$R^4$ is selected from isobutyryl, pivaloyl and optionally substituted benzoyl, preferably benzoyl.

It is strongly emphasised that novel derivatives characterized by general formula 2C can be considered as sole chemical entities such as either α or β anomers, preferably the β anomer, or even an anomeric mixture of α and β isomers. Novel 6'-SL intermediates of general formula 2C can be characterized as crystalline solids, oils, syrups, precipitated amorphous material or spray dried products, preferably as crystalline solids. If crystalline, compounds of general formula 2C might exist either in anhydrous or in hydrated crystalline forms by incorporating one or several molecules of water into their crystal structures. Similarly, novel compounds characterized by general formula 2C might exist as crystalline substances incorporating ligands such as organic molecules and/or ions into their crystal structures.

Novel compounds of general formula 2C provided by the present invention can be used for the preparation of 6'-SL itself and other 6'-SL derivatives by using chemical/enzymatic methodologies known in the Art. Novel compounds of general formulae 2C can also be used as advanced precursors/intermediates for the production/preparation of numerous human milk oligosaccharides. Novel compounds of general formulae 2C can also be considered as valuable intermediates for the synthesis of complex oligosaccharides/glycoconjugates suitable for therapeutic/nutritional use.

Another aspect of the present application relates to providing compounds of general formula 2D

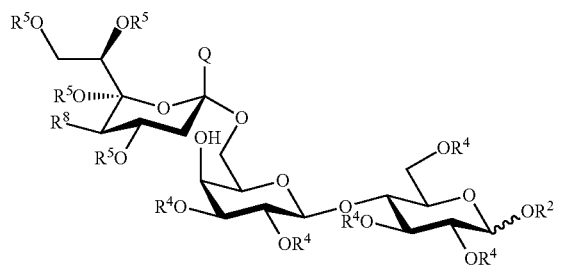

general formula 2D wherein $R^2$ is a group removable by catalytic hydrogenation,
$R^4$ is selected from benzyl substituted by 1-3 methoxy group(s) and H,
$R^5$ is selected from optionally substituted acyl and H,
$R^8$ is selected from —NHAc and NAc$_2$, and
Q is selected from —COO-alkyl, which alkyl is optionally substituted and —COOH in either protonated or deprotonated form,
provided that if Q is —COOH in either protonated or deprotonated form and $R^8$ is —NHAc, then both $R^4$ and $R^5$ cannot be H simultaneously.

It is strongly emphasised that novel derivatives characterized by general formula 2D can be considered as sole chemical entities such as either α or β anomers, preferably the β anomer, or even an anomeric mixture of α and β isomers. Novel 6'-SL intermediates of general formula 2D can be characterized as crystalline solids, oils, syrups, precipitated amorphous material or spray dried products, preferably as crystalline solids. If crystalline, compounds of general formula 2D might exist either in anhydrous or in hydrated crystalline forms by incorporating one or several molecules of water into their crystal structures. Similarly, novel compounds characterized by general formula 2D might exist as crystalline substances incorporating ligands such as organic molecules and/or ions into their crystal structures.

In a preferred embodiment —OR$^2$ is in β, $R^2$ is selected from benzyl, 4-methylbenzyl, 4-chlorobenzyl and 1-naphthylmethyl, $R^4$ and $R^5$ are H, $R^8$ is —NHAc and Q is —COO-alkyl, which alkyl is optionally substituted, preferably —COOMe.

Novel compounds of general formula 2D provided by the present invention can be used for the preparation of 6'-SL itself and other 6'-SL derivatives by using chemical/enzymatic methodologies known in the Art. Novel compounds of general formulae 2D can also be used as advanced precursors/intermediates for the production/preparation of numerous human milk oligosaccharides. Novel compounds of general formulae 2D can also be considered as valuable intermediates for the synthesis of complex oligosaccharides/glycoconjugates suitable for therapeutic/nutritional use.

It has to be emphasized that compounds of general formula 4A are novel. Thus the present invention provides compounds of general formula 4A

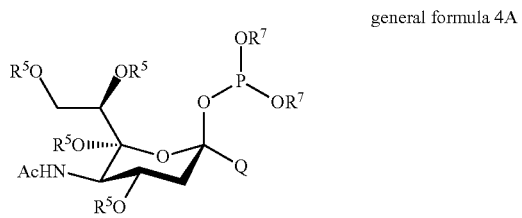

general formula 4A wherein $R^5$ is optionally substituted acyl, Q is —COO-alkyl, which alkyl is optionally substituted and $R^7$ is substituted benzyl. In preferred embodiments $R^5$ is acetyl, Q is —COOCH$_3$ and $R^7$ is substituted benzyl, preferably substituted by chloro or bromo in position 4.

Compounds of general formula 4A can be considered as crystalline materials in β-anomeric form. They are stable, can be stored for longer period of time without significant decomposition, can be easily activated in glycosylation reactions and shows excellent α-selectivity. As their unsubstituted benzyl phosphite counterparts are known not to be solid, compounds of general formula 4A according to the present application has obviously advantageous applicability in sialylation reactions.

Accordingly, the present invention provides the use of compounds of general formula 4A in the synthesis of sialooligosaccharides, preferably sialylated human milk oligosaccharides. Such sialylated HMOs are e.g. 6'-sialyllactose, 3'-sialyllactose, 3'-sialyl-3-fucosyllactose, disialyllacto-N-tetraose, disialyl monofucosyllacto-N-hexaose, sialyllacto-N-tetraose a, sialyllacto-N-tetraose b, sialyllacto-N-tetraose c, sialyllacto-N-fucopentaose II, monofucosyl monosialyl-lacto-N-hexaose I, monosialyllacto-N-neohexaose I, monosialyl monofucosyllacto-N-neohexaose.

The present invention relates to also the production of compounds of general formula 4A (Scheme 3.). The readily available sialic acid derivatives according to general formula 9 are phosphitylated either by directly with $(R^{7O})_2PY$, in which Y is halogen or dialkylamino group, in the presence of tertiary amine, preferably Et$_3$N, in aprotic solvent, preferably dichloromethane, or in two consecutive steps: first adding PCl$_3$ then $R^7$OH($R^7$ is substituted benzyl, preferably halo- or methylbenzyl). In both steps a tertiary amine base is needed to neutralize the hydrochloric acid formed: in the first step imidazole, in the second step Et$_3$N are the preferred base. The solvent used is selected from aprotic solvents, preferably dichloromethane is the solvent of choice.

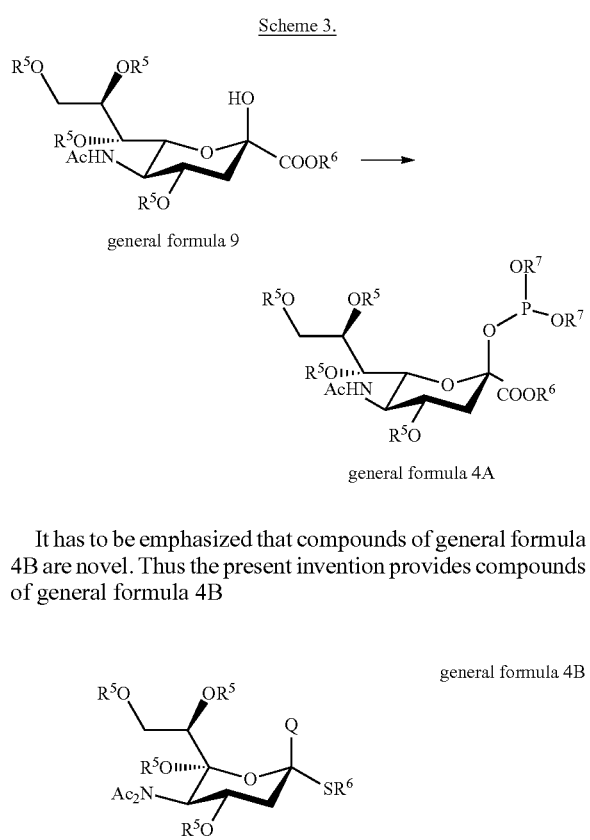

Scheme 3.

general formula 9 general formula 4A

It has to be emphasized that compounds of general formula 4B are novel. Thus the present invention provides compounds of general formula 4B general formula 4B wherein $R^5$ is optionally substituted acyl, preferably acetyl, $R^6$ is selected from $C_{2-6}$ alkyl, $C_{3-6}$ cycloalkyl and optionally substituted benzyl, preferably from ethyl, isopropyl, t-butyl, benzyl and cyclohexyl,
Q is —COO-alkyl, which alkyl is optionally substituted, preferably —COOMe.

Compounds of general formula 4B can be considered as crystalline materials in α-anomeric form. They are stable, can be stored for longer period of time without significant decomposition, can be easily activated in glycosylation reactions and shows excellent α-selectivity. As their analogues such as methyl, phenyl or 4-methylphenyl thioglycoside are known not to be solid, compounds of general formula 4B according to the present application has obviously advantageous applicability in sialylation reactions.

Accordingly, the present invention provides the use of compounds of general formula 4B in the synthesis of sialooligosaccharides, preferably sialylated human milk oligosaccharides. Such sialylated HMOs are e.g. 6'-sialyllactose, 3'-sialyllactose, 3'-sialyl-3-fucosyllactose, disialyllacto-N-tetraose, disialyl monofucosyllacto-N-hexaose, sialyllacto-N-tetraose a, sialyllacto-N-tetraose b, sialyllacto-N-tetraose c, sialyllacto-N-fucopentaose II, monofucosyl monosialyllacto-N-hexaose I, monosialyllacto-N-neohexaose I, monosialyl monofucosyllacto-N-neohexaose.

The present invention relates to also the production of compounds of general formula 4B. Sialic acid ester or tetra-O-acetyl sialic acid ester can be acetylated with isopropenyl acetate is the presence of acid, preferably tosic acid, at elevated temperature. The resulting 2,4,7,8,9-penta-O-acetyl-5-(N-acetylacetamido)-3,5-dideoxy-2-thio-D-glycero-D-galacto-non-2-ulopyranosonate is then reacted with $R^6SH$ ($R^6$ is $C_{2-6}$ alkyl, $C_{3-6}$ cycloalkyl or optionally substituted benzyl, preferably ethyl, isopropyl, t-butyl, benzyl or cyclohexyl) to form compounds of general formula 4B under Lewis acid (e.g. boron trifluoride etherate, TfOH, TMSOTf, etc.) activation in an aprotic solvent or in mixture of aprotic solvents like dichloromethane, dichloroethane, chloroform, THF, dioxane, acetonitrile, DMF, etc. Activated alkylthio derivatives like trimethylsilyl-$SR^6$ can be also applied. According to a different approach tetraacetyl sialyl chloride can be coupled with $R^6SH$ in the presence of base and the resulting thioglycoside can be subsequently N-acetylated with isopropenyl acetate (Scheme 4.).

Scheme 4.

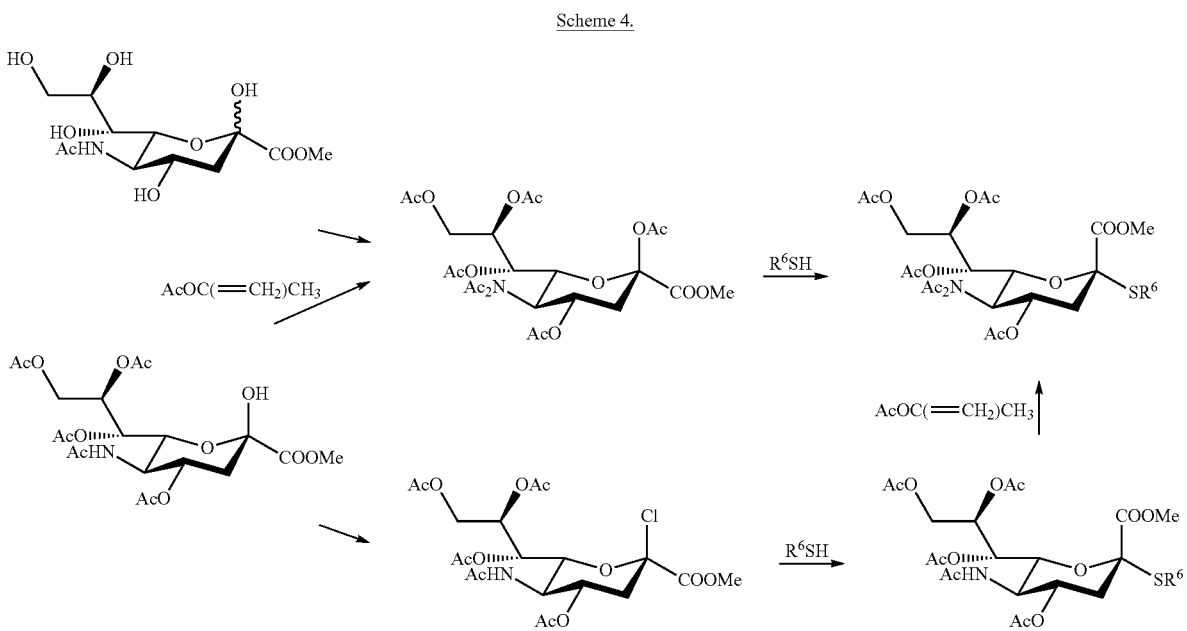

It has to be emphasized that the use compounds of general formula 4C in sialylation reactions has not been mentioned in the art. Thus the present invention provides compounds of general formula 4C for use as sialyl donor

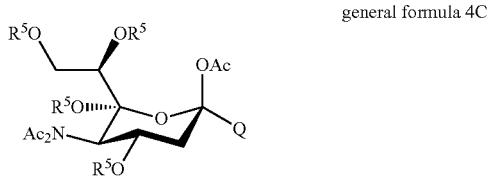

general formula 4C wherein $R^5$ is optionally substituted acyl, preferably acetyl and Q is —COO-alkyl, which alkyl is optionally substituted, preferably —COOMe.

Compounds of general formula 4C can be considered as crystalline materials in β-anomeric form. They are stable, can be stored for longer period of time without significant decomposition, can be easily activated in glycosylation reactions and shows excellent α-selectivity.

Accordingly, in a more preferred embodiment the present invention provides the use of compounds of general formula 4C in the synthesis of sialooligosaccharides, preferably sialylated human milk oligosaccharides. Such sialylated HMOs are e.g. 6'-sialyllactose, 3'-sialyllactose, 3'-sialyl-3-fucosyllactose, disialyllacto-N-tetraose, disialyl monofucosyllacto-N-hexaose, sialyllacto-N-tetraose a, sialyllacto-N-tetraose b, sialyllacto-N-tetraose c, sialyllacto-N-fucopentaose II, monofucosyl monosialyllacto-N-hexaose I, monosialyllacto-N-neohexaose I, monosialyl monofucosyllacto-N-neohexaose.

It is emphasised that compounds of general formula 3A are novel, crystalline, they can be considered as sole chemical entities such as α- or β-anomers or even an anomeric mixture thereof, preferably in β-anomer. They might exist in anhydrous, hydrated as well as solvated forms.

Thus the present invention provides compounds of general formula 3A

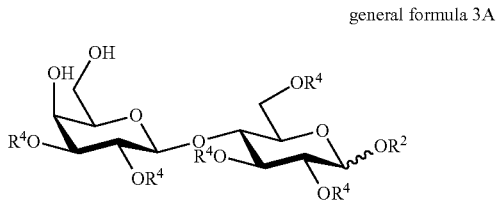

general formula 3A wherein $R^2$ is a group removable by catalytic hydrogenation, and
$R^4$ is selected from benzyl substituted by 1-3 methoxy group(s) and optionally substituted acyl provided that acetyl is excluded.

In a more preferred embodiment —$OR^2$ is in β, $R^2$ is selected from benzyl, 4-methylbenzyl, 4-chlorobenzyl and 1-naphthylmethyl, and $R^4$ is selected from isobutyryl, pivaloyl and benzoyl.

The present inventors realized that acetyl groups are inconvenient protective groups when compounds of general formula 3A act as glycosyl acceptor in sialylation reactions. Under the conditions of coupling acetyl migration always occurred to give complex mixture containing substances with similar physical characteristics which compounds can be separated only by lengthy and/or sophisticated and/or laborious techniques, e.g. chromatography. Choosing bulkier acyl protective group that don't tend or tend less to migrate results in an acceptor whose coupling product is formed almost exclusively in glycosidation, making the work-up procedure and isolation process of the desired compounds simpler, quick, powerful and cost-effective, e.g. by crystallization, which is one of the paramount concerns in large scale preparation or industrial process.

Another aspect of the present invention is to prepare glycosyl acceptor derivatives characterized by general formula 3A above (Scheme 5.). The starting O-lactoside can be easily formed by Fischer glycosidation (lactose treated with the corresponding alcohol in the presence of acid catalysts). The so obtained O-lactosides of general formula 6 are then protected selectively at the 4',6'-position with $R^9$—CHO ($R^9$=phenyl optionally substituted with 1-2 alkoxy or nitro), benzophenone or di-O-acetals thereof in known manner giving rise to compounds of general formula 7 followed by acylation or methoxy-benzylation to obtain compounds of general formula 8. The acylation can be performed with acyl halides, anhydrides, active esters etc. in the presence of base in known manner. A typical benzyl ether formation runs by adding the appropriate benzyl halogenide (chloride, bromide or iodide) and NaH or powdered KOH or NaOH in an inert organic aprotic solvent like THF, dioxane, DMF, etc., even the reagent benzyl halogenide can be used as solvent. Phase-transfer catalysis conditions can be also applied in benzylation, the organic phase solvent is selected from the group of aromatic hydrocarbons (toluene, benzene, xylols) and basic aqueous solution, preferably 50% NaOH or KOH solution is used as aqueous phase. Quaternary ammonium or phosphonium salts, or crown ethers can be added as catalyst, preferably TBAI. Removal of the acetal or ketal type protecting group from compounds of general formula 8 by acidic hydrolysis results in compounds of general formula 3A.

Scheme 5.

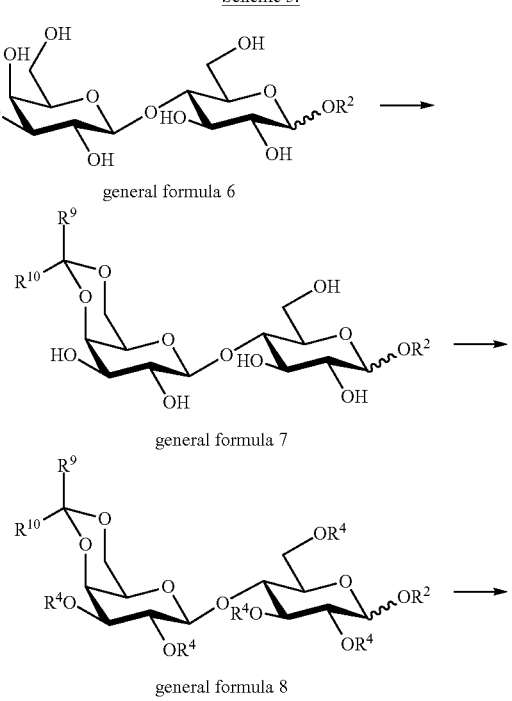

general formula 6 general formula 7 general formula 8

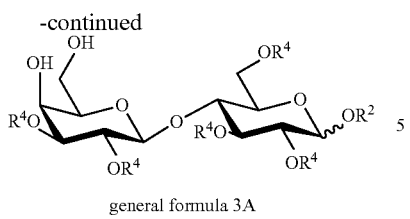

general formula 3A

In a preferred embodiment of preparing compounds of general formula 3A β-benzyllactoside is used as starting material ($R^1$=OBn in general formula 6). In a further preferred realization benzaldehyde-dimethylacetal is the reagent for protecting 4',6'-positions. To protect the free hydroxyls in compounds of general formula 7 pivaloyl and optionally substituted benzoyl groups are favoured. In case of removing benzylidene acetal from compounds of general formula 8 diluted strong inorganic acids, organic acids (e.g. alkanoic acids, sulfonic acids) and H$^+$ form ion exchange resin are given preference as acid catalyst, preferably p-toluenesulfonic acid, and among the solvents alcohols, aromatic hydrocarbons, chlorinated alkanes or mixtures thereof are favourable, preferably DCM, methanol or mixtures thereof.

According to a further aspect the compounds of general formula 3A defined and claimed above can be used for preparing 6'-SL. Compounds of general formula 3A as acceptor reacts readily with any suitable sialyl donor giving rise to protected 6'-SL intermediates according to general formula 2 above, which can then be transformed into 6'-SL and salts thereof by means of deprotective manipulations as described above.

Other features of the invention will become apparent in the course of the following descriptions of exemplary embodiments which are given for illustration of the invention and are not to be limiting thereof.

EXAMPLES

Example 1

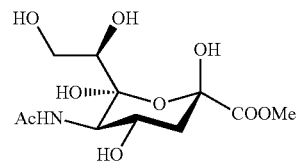

A mixture of anhydrous sialic acid (100 g, 323 mmol) and dried Amberlite IR-120 (H$^+$) ion exchange resin (100 g) in MeOH (1500 mL) was stirred for 15 hours at RT. The ion exchange resin was filtered off and washed with MeOH (2×100 mL). The washes were combined with the filtrate and concentrated to 300 mL. The concentrated residue crystallized upon seeding at RT. The crystals were collected by filtration giving 73.8 g (71%) sialic acid methyl ester. The mother liquor was concentrated (10.5 g) and recrystallized from MeOH (30 mL) to yield 7.4 g (7%) sialic acid methyl ester. Total yield 81.2 g (78%).

$^1$H NMR (D$_2$O) δ in ppm: 1.89 (dd, 1H, J=13.0 Hz, J=11.4 Hz); 2.03 (s, 3H); 2.28 (dd, 1H, J=13.0 Hz, J=4.7 Hz); 3.52 (dd, 1H, J=8.9 Hz, J=3.0 Hz); 3.59 (dd, 1H, J=11.6 Hz, J=6.1 Hz); 3.71 (ddd, J=8.9 Hz, J=2.5 Hz, J=11.6 Hz); 3.82 (dd, 1H, J=11.6 Hz, J=2.5 Hz); 3.82 (s, 3H); 3.90 (dd, 1H, J=10.1 Hz, J=10.0 Hz); 3.98-4.10 (m, 2H, H-6, H-4).

Example 2

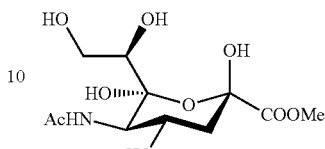

To a suspension of anhydrous sialic acid (100 g, 323 mmol) in MeOH (1200 ml) [0.03% water content] 8% HCl in MeOH (50 ml) was added and the reaction mixture was stirred for 6 hours at RT. The reaction mixture was neutralized with triethylamine (15 ml) and the clear solution was concentrated to 270 mL. The concentrated residue crystallized upon seeding at RT for 2 hours. The solid was collected by filtration yielding 104.9 g (100%).

Example 3

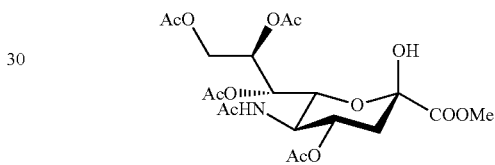

A suspension of sialic acid methyl ester (50 g, 155 mmol) and acetic anhydride (73 ml, 775 mmol) in DCM (175 mL) was stirred at RT and 70% perchloric acid (1 mL) was then added dropwise within 30 minutes. During the addition the temperature of the mixture increased until reflux. The reaction mixture was stirred at reflux for 2.5 h, and after this time MeOH (7.5 ml, 185 mmol) was added dropwise and the reaction mixture was stirred for a further hour at RT. The reaction mixture was diluted with DCM (175 mL) and washed with water (3×50 mL). The combined water phases were extracted with DCM (2×100 mL). The combined organic phases were washed with saturated NaHCO$_3$ (2×100 mL) and evaporated. The residue (59.6 g) was dissolved in iBuOAc at 50° C. and the mixture was cooled down to RT and let overnight complete the crystallization. The solid was collected by filtration yielding 39.2 g (52%) of tetraacetyl sialic acid methyl ester.

$^1$H NMR(C$_6$D$_6$) δ in ppm: 1.60, 1.63, 1.70, 1.85, 1.92 (5s, 15H); 2.19 (dd, 1H, J=12.8 Hz, J=5.7 Hz); 2.25 (ddd, 1H, J=12.8 Hz, J=10.8 Hz); 3.28 (s, 3H); 4.23 (dd, 1H, J=12.4 Hz, J=7.6 Hz); 4.26 (dd, 1H); 4.54 (ddd, 1H, J=10.8 Hz); 4.78 (d, 1H, J=10.2 Hz); 5.02 (dd, 1H, J=12.4 Hz, J=2.0 Hz); 5.26 (ddd, 1H, J=10.8 Hz, J=5.7 Hz, J=10.5 Hz); 5.61 (ddd, 1H, J=2.0 Hz, J=7.6 Hz); 5.64 (dd, 1H, J=2.3 Hz, J=4.2 Hz).

$^1$H(CDCl$_3$) δ in ppm: 1.91, 2.02, 2.03, 2.11, 2.15 (5s, 15H); 2.19 (dd, 1H, J=12.8 Hz, J=11.4 Hz); 3.26 (ddd, 1H, J=12.8 Hz, J=5.4 Hz); 3.86 (s, 3H); 4.03 (dd, 1H, J=12.4 Hz, J=7.5 Hz); 4.13-4.21 (m, 2H); 4.51 (dd, 1H, J=12.4 Hz, J=2.4 Hz); 5.22 (ddd, 1H, J=11.4 Hz, J=5.4 Hz, J=9.5 Hz); 5.25 (ddd, 1H, J=2.4 Hz, J=7.5 Hz, J=5.6 Hz); 5.36 (dd, 1H, J=1.5 Hz, J=5.6 Hz); 5.71 (m, 1H).

$^{13}$C NMR: 20.65, 20.75, 20.93, 22.93, 36.11, 49.04, 53.18, 62.50, 68.3, 69.12, 71.32, 72.07, 94.84, 168.93, 170.12, 170.30, 170.72, 171.04, 171.43

Example 4

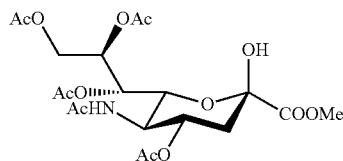

To a mixture of sialic acid methyl ester (60.8 g, 188 mmol) and acetic anhydride (89 ml, 940 mmol) in DCM (220 mL), perchloric acid 70% (1.22 mL) was added dropwise within 30 minutes. During the addition the temperature of the mixture increased until reflux. The reaction mixture is stirred at reflux for 2.5 h. Subsequently, MeOH (9.2 mL, 225 mmol) was added dropwise and the reaction mixture was stirred for one additional hour at RT. The clear solution was added dropwise to a suspension of Na$_2$CO$_3$ (60.8 g; 573 mmol) in DCM and the mixture was stirred at room temperature for 2 hours. The remaining solid was removed by filtration and was washed with DCM (2×50 mL). The combined DCM phase was concentrated to 150 ml, $^i$BuOAc (150 mL) was added and the remaining DCM was removed and let crystallize overnight. The crystals were collected by filtration yielding 65 g (71%) of tetraacetyl sialic acid methyl ester.

Example 5

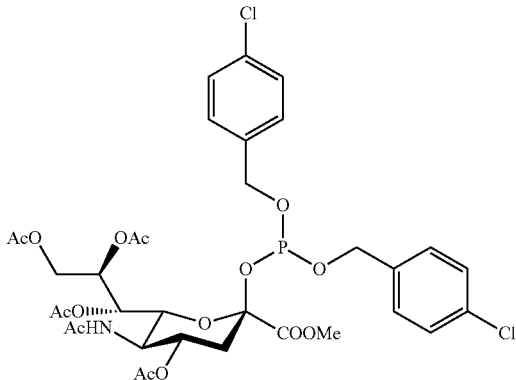

A suspension of imidazole (1.88 kg) in DCM (20 L) was cooled down to 5° C., PCl$_3$ (690 ml) was added, followed by the addition of Et$_3$N (4.16 L). The heavy slurry was stirred for 60 min. at 0° C. and the tetraacetate (2.59 Kg) was added in DCM solution (3 liter/kg). The temperature was set to 25° C. and the reaction mixture stirred for 3 h. After this time p-Cl-benzyl alcohol (2.64 Kg) was added as solid and the reaction mixture stirred for another 2 h. The reaction mixture was transferred to the 110 L extraction vessel, was neutralized with 1N HCl (26 L) and the phases were separated. The organic phase was concentrated to an oil and kept in the fridge until next day. The residue was dissolved in 15 L of BuOMe and washed with water (3×7 L); the organic phase was the evaporated. The residue was dissolved in i-Pr$_2$O (5 L) and the turbid solution turned into a solid after. The slurry was filtered off, the solid was washed with i-Pr$_2$O (2×1.5 L) and dried in the vacuum oven. (2.65 Kg with 95% purity).

$^1$H NMR δ (CDCl$_3$) in ppm: 1.9-2.15 (m, 16H); 2.39 (dd, 1H, J=4.9 Hz, J=13.00 Hz); 3.75 (s, 3H); 3.85 (dd, 1H, J=10.6 Hz, J=2.00 Hz); 4.05 (m, 1H); 4.15 (dd, J=7.4, J=12.4); 4.6 (m, 2H); 4.8-5 (m, 4H); 5.15 (m, 2H); 5.22 (m, 1H).

Example 6

Analogously Prepared

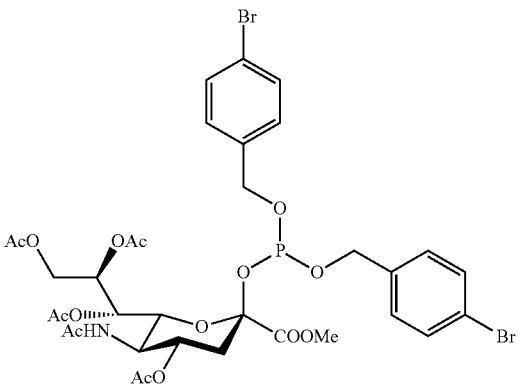

Example 7

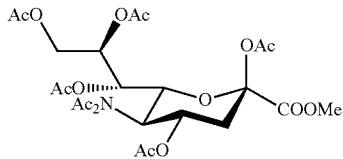

Method A: To a suspension of the N-acetyl neuraminic acid methyl ester tetra-O-acetate (100 g, 0.2 mol) in isopropenyl acetate (300 mL) TsOH was added and the reaction mixture was stirred for 16 h at 75° C. (oil bath). The reaction became a clear solution after couple of minutes. When TLC (toluene/acetone 3/2) showed completion the mixture was cooled, diluted with 500 mL of EtOAc and washed as follows: 1× NaHCO$_3$ (500 mL), 1× H$_2$O (500 mL) and 1× brine (300 mL). The residue was concentrated in vacuo, redissolved in EtOAc (200 mL) and heptane (280 mL) was added at 70° C. The mixture was cooled to 0° C. and stirred for 2 h. The solid was collected by filtration to yield 102.12 g (87%).

Method B: To a suspension of sialic acid methyl ester (100 g) in isopropenyl acetate (500 mL) TsOH was added and the reaction mixture stirred for 16 h at 75° C. (oil bath). The reaction became a clear solution after couple of hours. When TLC (toluene/acetone 3/2) showed completion the mixture was cooled, diluted with 500 mL of EtOAc and washed as follows: 1× NaHCO$_3$ (500 mL), 1× H$_2$O (500 mL) and 1× brine (300 mL). The residue was concentrated in vacuo, redissolved in EtOAc (200 mL) and heptane (280 mL) was added at 70° C. The mixture was cooled to 0° C. and stirred for 2 h. The solid was collected by filtration to yield 101.3 g (85%).

$^1$H NMR (CDCl$_3$) δ (ppm): 1.95-2.23 (m, 16H); 2.31 (s, 3H); 2.39 (s, 3H); 2.66 (dd, 1 h, J=13.5 Hz, J=6.3 Hz); 3.77 (s, 3H); 4.15 (m, 2H); 4.35 (dd, 1H, J=2.4 Hz, J=12.4 Hz); 5.15 (m, 3H); 5.8 (m, 1H).

$^{13}$C NMR (CDCl$_3$) δ (ppm): 20.97, 21.13, 26.13, 28.24, 53.36, 54.66, 57.26, 62.03, 66.56, 67.72, 69.93, 70.57, 97.37, 166.80, 168.78, 169.80, 169.98, 170.49, 173.82

Example 8

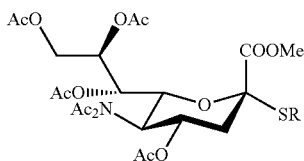

To a 0° C. cold solution of N,N-diacetyl neuraminic acid methyl ester penta-O-acetate (10 g, 17.4 mmol) and RSH (2.2 eq) in DCM (50 mL) BF$_3$.OEt$_2$ (2.79 mL, 1.3 eq) was added and the reaction mixture was stirred at this temperature for 3 h (overnight in the case of tBuSH). Aqueous NaHCO$_3$ was added to neutralize (25 mL) the acid and the phases were separated, the organic phase was then washed with water, and the solvent was evaporated in vacuo. The residue was crystallized as follows.

R=i-Pr (crystallized from i-Pr$_2$O) yield 75%, mp: 110-111° C.

$^1$H NMR (CDCl$_3$) δ (ppm): 1.25 (d, 3H, J=6.7 Hz); 1.35 (d, 3H, J=7 Hz); 1.9-2.2 (m, 13H); 2.3 (s, 3H); 2.4 (s, 3H); 2.65 (dd, 1H, J=5.1 Hz, J=13.7 Hz); 3.25 (m, 1H); 3.8 (s, 3H); 4.2 (m, 2H); 4.75 (dd, 1H, J=2.3 Hz, J=12.4 Hz); 5.1 (m, 1H); 5.25 (dd, 1H, J=2.5 Hz, J=3 Hz); 5.45 (dd, 1H, J=9.9 Hz, J=2.25 Hz); 5.8 (m, 1H).

$^{13}$C NMR (CDCl$_3$) δ (ppm): 20.88, 20.90, 21.04, 21.11, 24.83, 25.01, 26.13, 28.11, 34.29, 39.18, 52.98, 57.56, 62.59, 67.09, 69.16, 69.68, 72.57, 85.43, 169.18, 169.63, 170.35, 170.56, 170.58, 173.75, 174.49.

R=Bn (crystallized from MeOH) yield 79%

$^1$H NMR (CDCl$_3$) δ (ppm): 1.9-2.2 (m, 13H); 2.3 (s, 3H); 2.4 (s, 3H); 2.7 (dd, 1H, J=5.1 Hz, J=13.9 Hz); 3.5 (s, 3H); 3.8 (s, 2H); 4.2 (m, 2H); 4.7 (dd, 1H, J=2.4 Hz, J=12.4 Hz); 5.2 (m, 1H); 5.3 (dd, 1H, J=2 Hz, J=4.2 Hz); 5.55 (dd, 1H, J=9.9 Hz, J=2 Hz); 5.8 (m, 1H); 7.3 (m, 5H).

$^{13}$C NMR (CDCl$_3$) δ (ppm): 20.91, 20.94, 21.09, 21.11, 26.16, 28.18, 32.99, 38.63, 52.80, 57.59, 62.36, 67.16, 68.65, 69.53, 71.82, 85.17, 127.41, 128.71, 129.009, 136.45, 168.43, 169.65, 170.39, 170.50, 170.66, 173.71, 174.55.

R=t-Bu (crystallized from i-Pr$_2$O/Heptane) yield 80%, mp: 95-98° C.

$^1$H NMR (CDCl$_3$) δ (ppm): 1.4 (s, 9H); 1.9-2.2 (m, 13H); 2.3 (s, 3H); 2.4 (s, 3H); 2.7 (dd, 1H, J=4.8 Hz, J=13.5 Hz); 3.8 (s, 3H); 4.2 (m, 2H); 4.7 (dd, 1H, J=1.5 Hz, J=12.2 Hz); 5.1 (m, 1H); 5.3 (dd, 1H, J=2.8 Hz, J=3.2 Hz); 5.55 (dd, 1H, J=10 Hz, J=2.7 Hz); 5.8 (m, 1H); 7.3 (m, 5H).

$^{13}$C NMR (CDCl$_3$) δ (ppm): 20.87, 20.88, 21.02, 21.09, 26.07, 28.09, 31.46, 41.58, 47.81, 52.90, 57.77, 62.76, 66.99, 69.35, 69.50, 72.62, 86.45, 169.55, 169.81, 170.38, 170.61, 170.72, 174.02, 174.56.

R=Et (crystallized from i-Pr$_2$O) yield 78%, mp: 137-138° C.

R=cyclohexyl (crystallized form MeOH) yield 78%, mp: 146-147° C.

$^1$H NMR (CDCl$_3$) δ (ppm): 1.2-1.8 (m, 12H); 1.9-2.2 (m, 13H); 2.3 (s, 3H); 2.4 (s, 3H); 2.65 (dd, 1H, J=5.2 Hz, J=13.8 Hz); 2.8 (m, 1H); 3.8 (s, 3H); 4.2 (m, 2H); 4.8 (dd, 1H, J=2.1 Hz, J=12.4 Hz); 5.05 (m, 1H); 5.25 (t, 1H, J=2.3 Hz); 5.45 (dd, 1H, J=9.9 Hz, J=2.3 Hz); 5.8 (m, 1H).

$^{13}$C NMR (CDCl$_3$) δ (ppm): 20.97, 20.99, 21.11, 21.15, 25.51, 26.23, 26.50, 28.16, 35.23, 35.29, 39.09, 42.05, 45.88, 53.01, 57.43, 63.05, 67.18, 69.53, 70.12, 73.33, 85.20, 169.32, 169.72, 170.45, 170.62, 170.68, 173.73, 174.51.

Example 9

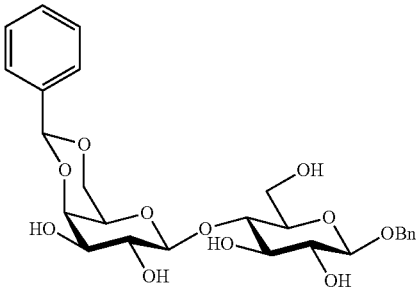

To a suspension of β-benzyllactoside (700 g, 1.6 mol) in DMF (5 L) was added benzaldehyde dimethylacetal (389.5 mL, 2.6 mmol, 1.6 eq.) and p-TsOH.H$_2$O (31.5 g, 0.17 mmol, 0.1 eq.). The reaction mixture was then heated to 40-44° C. for approximately 22 h, after which a white suspension was obtained. It was cooled to ice bath temperature, i-Pr$_2$O (4 L) was added and the resulting suspension was further stirred for 1½ h at this temperature. This mixture was filtrated and the white solid obtained was washed/suspended with i-Pr$_2$O (2×1 L). After drying 702 g were obtained of the wanted product as a white free solid. The resulting mother liquor was allowed to stand at room temperature for approximately 3 days, during which time more white solid appeared. This was filtrated and washed/suspended with $^{i-Pr}_2$O (2×150 mL). Obtained further 25 g of product. Combined amount: 727 g (86%).

$^1$H NMR δ (CD$_3$OD) in ppm: 3.3-3.45 (m, 2H); 3.5-3.7 (m, 5H); 3.95 (m, 2H); 4.15 (m, 3H); 4.40 (d, 1H, J=7.8 Hz); 4.5 (d, 1H, J=7.5 Hz); 4.65 (d, 1H, J=11.8 Hz); 4.9 (d, 1H, J=11.8 Hz); 5.55 (s, 1H); 7.25 (m, 5H).

$^{13}$C NMR: 61.75, 68.33, 70.17, 71.78, 71.86, 73.52, 74.89, 76.33, 77.35, 80.02; 102.3, 103.22, 104.87; 128.8-139.03

Example 10

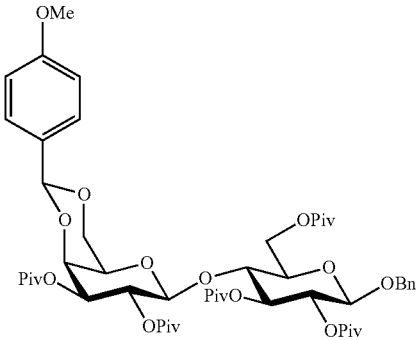

The starting pentaol (650 g, 1.16 mol), pyridine (3.25 l) and DMAP (7.1 g, 58 mmol) were loaded to the reactor and the PivCl (1.3 l, 10.6 mol) was added in one hour, the mixture was warmed up to 95° C. and stirred for 15 hours. The reaction mixture was cooled to 60° C., 4.63 l MeOH was added, and the mixture was stirred in room temperature for 1.5 hours. The solid was filtrated, washed two times with 1.5 l MeOH, dried on open air for one night and in vacuum for three days.

¹H NMR 6 (CD₃OD) in ppm: 1.05-1.2 (4s, 36H); 1.25 (s, 9H); 3.4 (m, 1H); 3.55 (m, 1H); 3.8 (s, 3H); 3.95 (t, 1H, J=9.5 Hz); 4.05 (dd, 1H, J=12.5 Hz, J=1.7 Hz); 4.2 (dd, 1H, J=11.8 Hz, J=5.5 Hz)); 4.35 (dd, 1H, J=12.5 Hz, J=0.9 Hz); 4.38 (dd, 1H, J=0.3 Hz, J=3.5 Hz); 4.55 (m, 4H); 4.8 (m, 2H); 4.95 (dd, 1H); 5.2 (m, 1H); 5.3 (m, 1H), 5.45 (s, 1H); 6.85 (m, 2H); 7.2-7.4 (m, 7H).

Example 11

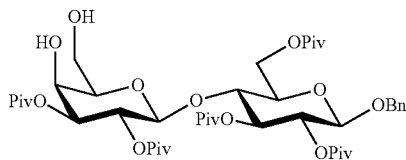

To a mixture of the starting material (example 10, 32.5 g, 33.5 mmol), DCM (65 ml) MeOH (16 ml) and water (6.5 ml), pTsOH.H₂O (2.6 g, 13.7 mmol) was added and then heated to reflux temperature. After two hours TLC (Toluene:Acetone 5:1) indicates the reaction is finished. The reaction mixture was cooled down to RT, diluted with DCM (65 ml) and washed with saturated NaHCO₃ (65 ml) and water (65 ml). The organic phase was dried over MgSO₄ and concentrated to get 33 g colourless oil. The crude product was dissolved in EtOAc (227 ml) at reflux temperature, petroleum ether (40-70° C., 70 ml) was added and the mixture was cooled to 0° C. The solid was filtrated, washed with petroleum ether (2×30 ml) and dried to get 22.6 g (79.2%) acceptor.

¹H NMR 6 (CD₃OD) in ppm: 1.05-1.2 (4s, 36H); 1.25 (s, 9H); 3.4 (m, 1H); 3.8 (m, 1H); 3.95 (m, 2H); 4.1 (m, 1H); 4.2 (dd, 1H, J=11.8 Hz, J=5.5 Hz); 4.55 (m, 4H); 4.8 (d, 1H, J=12.5 Hz); 4.9 (dd, 1H); 5.0 (dd, 1H); 5.2 (m, 2H); 7.2-7.4 (m, 5H).

Example 12

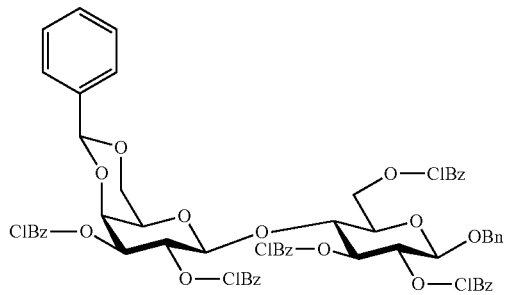

A solution of the pentaol (example 9, 5.6 g, 0.01 mol) in pyridine (20 mL) and DCM (50 mL) was cooled with ice bath and the p-chlorobenzoyl chloride (14 mL) was added slowly. The reaction mixture stirred for 24 h at RT, and the solvent was evaporated in vacuo. The residue was dissolved in DCM (70 mL) and washed with 1N HCl (40 mL), H₂O (40 mL), NaHCO₃ (40 mL) and brine (30 mL), The organic phase was dried over Na₂CO₃ and the solvent was evaporated in vacuo. The solid was dissolved in DCM (60 mL) and 360 mL MeOH were added. The white solid was filtrated and washed with MeOH and dried to yield 10.6 g (81%).

¹H NMR (CDCl₃) δ (ppm): 3.05 (m, 1H); 3.75 (m, 3H); 4.13 (dd, 1H, J=9.1 Hz, J=9.5 Hz); 4.31 (m, 1H); 4.42 (dd, 1H, J=4.1 Hz, J=12.0 Hz); 4.57 (m, 2H); 4.69 (d, 1H, J=7.7 Hz); 4.75 (d, 1H, J=7.9 Hz); 4.81 (d, 1H, 12.5 Hz); 5.15 (dd, 1H, J=3.5 Hz, J=10.4 Hz); 5.30 (s, 1H); 5.38 (dd, 1H, J=7.9 Hz, J=9.6 Hz); 5.75 (m, 2H) 7.05-8.05 (m, 30H).

¹³C NMR: 54.66, 62.92, 66.69, 68.13, 69.86, 70.76, 72.49, 72.73, 72.94, 73.13, 74.1, 76.42, 98.94, 100.81, 101.33, 126-140 (42C), 169.27, 164.46, 164.78, 165.13, 165.34.

Example 13

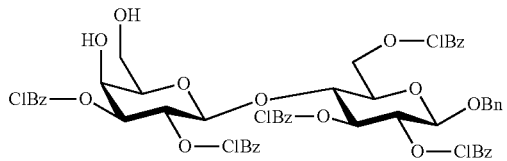

A solution of benzylidene acetal (example 12, 2.0 g, 1.65 mmol) in DCM/MeOH (4/1, 10 mL) and TsOH (126 mg) was stirred at 40° C. for 24 h. The reaction mixture was cooled to RT and diluted with DCM, washed with NaHCO₃, water and brine. The organic phase was dried over Na₂SO₄ and the solvent was removed in vacuo. The white solid was recrystallized form toluene to yield 1.28 g (70%).

¹H NMR (CDCl₃): 2.95 (m, 1H); 3.40 (m, 3H); 3.85 (m, 1H); 4.15 (m, 2H); 4.40 (dd, 1H, J=5 Hz, J=11.9 Hz); 4.5-4.8 (m, 5H); 5.15 (dd, 1H; J=3.1 Hz, 10.4 Hz); 5.40 (dd, 1H, J=7.7 Hz, J=9.4 Hz); 5.65 (m, 2H), 7.0-8.0 (m, 25H).

Example 14

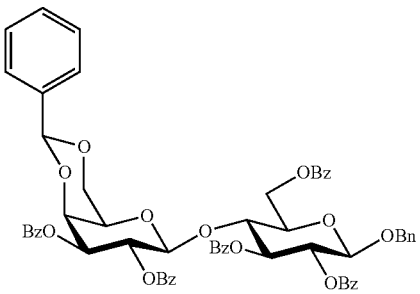

To an ice bath cooled solution of benzylidene-β-benzyllactoside (example 9, 6.2 g, 11.9 mmol) in pyridine (40 mL), BzCl (13.8 mL) was added dropwise. The reaction mixture stirred 30 min at this temperature, and overnight at RT. The reaction was quenched with MeOH and the solvent was evaporated in vacuo. The residue was dissolved in DCM and washed with water, 1N HCl, water, NaHCO₃, and brine. The organic phase was dried over Na₂SO₄ and the solvent was removed in vacuo. The solid obtained was recrystallized form EtOAc/Hexane to yield 9.1 g (73%) of a white pure solid. M.p.: 162-164° C.

¹H NMR (CDCl₃) δ (ppm): 2.95 (m, 1H); 3.58 (m, 1H); 3.78 (m, 2H); 4.25 (m, 2H); 4.40 (dd, 1H, J=4.3 Hz, J=12.1 Hz); 4.55 (d, 1H, 12.5 Hz); 4.65 (m, 1H); 4.70 (d, 1H, J=7.7 Hz); 4.78 (d, 1H, 12.5 Hz); 4.85 (d, 1H, J=7.9 Hz); 5.15 (dd, 1H, J=3.4 Hz, J=10.4 Hz); 5.30 (s, 1H); 5.40 (dd, 1H, J=7.8 Hz, J=9.2 Hz); 5.75 (m, 2H) 7.05-8.05 (m, 35H).

Example 15

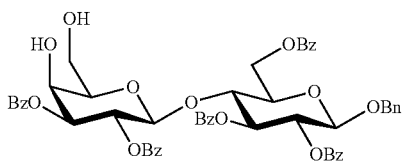

To a solution of the pentabenzoyl derivative (example 14, 22.0 g, 21 mmol) in DCM (140 mL) MeOH (20 mL) mixture TsOH monohydrate (1.6 g, 0.4 eq) was added, and the reaction mixture stirred for 2 days at 40° C. After this time a saturated solution of NaHCO$_3$ was added and the mixture stirred for 15 min. The phases were separated and the organic one was washed with water and brine; after drying over Na$_2$SO$_4$. The solvent was evaporated in vacuo and the solid obtained was suspended in EtOAc (200 mL) and the slurry stirred overnight, after filtration and drying 14.5 g (74%) were obtained. Mp.: 220-222.5° C.

$^1$H NMR (CDCl$_3$): 2.95 (m, 1H); 3.35 (m, 3H); 3.80 (m, 1H); 4.20 (m, 2H); 4.40 (dd, 1H, J=5 Hz, J=11.9 Hz); 4.5-4.9 (m, 5H); 5.07 (dd, 1H; J=3.1 Hz, 10.4 Hz); 5.45 (dd, 1H, J=7.7 Hz, J=9.4 Hz); 5.70 (m, 2H), 7.0-8.1 (m, 30H).

Example 16

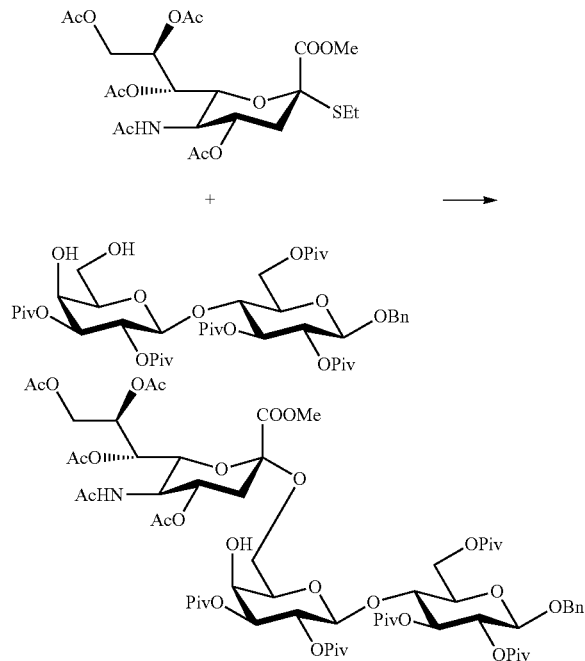

To a −40° C. cooled solution of the mixture donor-acceptor (100 g of the acceptor and 107 g of the donor) in CH$_3$CN/DCM 1/1 (1200 mL), NIS (78 g) was added and the mixture was stirred for 15 min at this temperature. After this time TfOH (5.1 mL) was added and the reaction was stirred between −40 and −50° C. for 2 h. Et$_3$N was then added (35 mL) and the solution was diluted with EtOAc (750 mL) and Na$_2$S$_2$O$_3$ (750 mL) was added and the solution was stirred until light yellow colour. The mixture was washed with Na$_2$S$_2$O$_3$ (750 mL) and brine (500 mL). The organic phase was dried over MgSO$_4$ and evaporated in vacuo. The crude was crystallized in 3L of TBME to give 80 g in two crops.

$^1$H NMR δ (CD$_3$OD) in ppm: 1.05-1.3 (m, 45H); 1.75-2.25 (m, 16H); 2.6 (dd, 1H, J=4.5 Hz, J=12.7 Hz); 3.5-3.75 (m, 8H); 3.9-4.10 (m, 5H), 4.3 (m, 2H); 4.5 (m, 4H); 4.75-5 (m, 4H); 5.2 (m, 3H); 5.3 (m, 2H); 7.25 (m, 5H).

$^{13}$C NMR: 21.02; 21.1; 21.32; 23.09; 23.45; 27.33; 27.38; 27.43; 27.51; 38.90; 39.08; 53.24; 62.34; 62.68; 62.70; 62.72; 66.44; 67.46; 68.87; 69.09; 69.4; 70.56; 71.78; 71.83; 73.00; 73.13; 73.43; 73.54; 73.88; 73.89; 99.26; 99.38; 99.92; 128.17; 128.57; 136.84; 168.09; 170.38; 170.41; 171.00; 171.22; 178.00.

Example 17

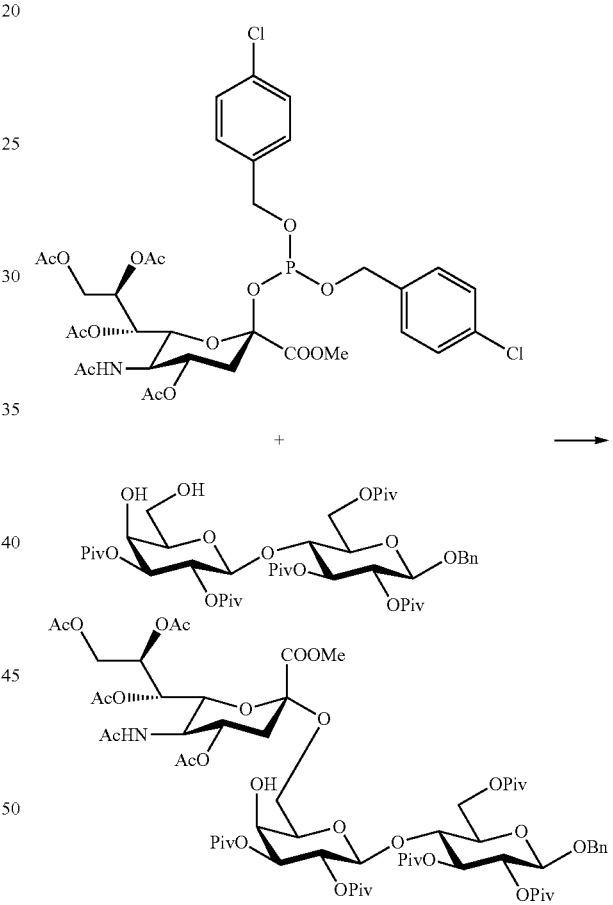

To a −40° C. cooled solution of the mixture donor-acceptor (acceptor: 5.3 g, donor: 8.5 g) in CH$_3$CN/DCM 1/1 (65 mL) TMSOTf (0.186 mL, 0.16 eq.) in 2 mL of MeCN was added. The reaction mixture was stirred for 3 h between −35-−40° C. and after this time Et$_3$N was added to neutralize the acid. The solution was diluted with 30 mL EtOAc and the organic phase was washed with 30 mL of water and 40 mL of brine, the organic phase was dried over Na$_2$SO$_4$ and the solvent was evaporated in vacuo. The residue was dissolved in 20 mL $^t$BuOAc at 70° C. and 70 mL i-Pr$_2$O were added. The solution crystallized overnight at 4° C. The crystals were collected by filtration and washed with i-Pr$_2$O to yield 4.3 g of pure product (51%).

Example 18

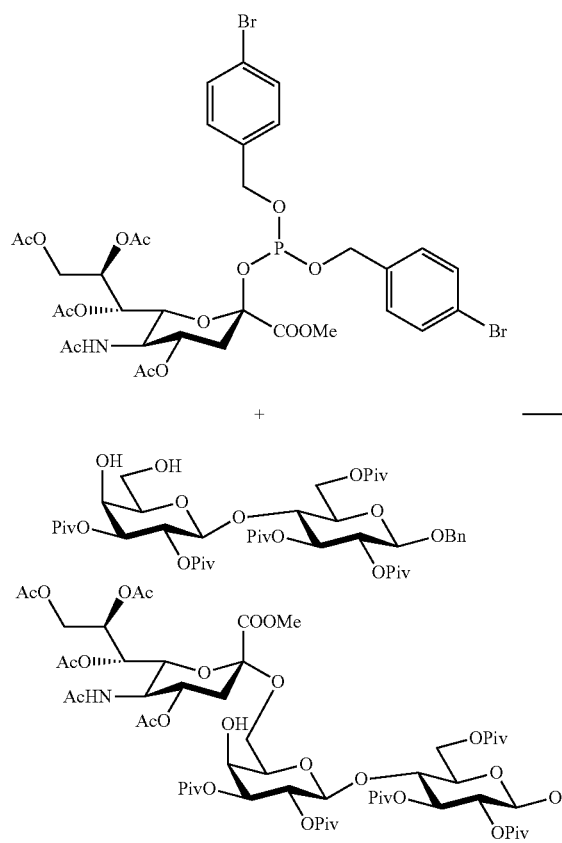

To a −40° C. cooled solution of the mixture donor-acceptor (acceptor: 5.3 g, donor: 9.42 g) in CH₃CN/DCM 1/1 (65 mL) TMSOTf (0.186 mL) in 2 mL of MeCN was added. The reaction mixture was stirred for 3 h between −35−−40° C. and after this time Et₃N was added to neutralize the acid. The solution was diluted with 30 mL EtOAc and the organic phase was washed with 30 mL of water and 40 mL of brine, the organic phase was dried over Na₂SO₄ and the solvent was evaporated in vacuo. The residue was dissolved in 20 mL ᵗBuOAc at 70° C. and 70 mL i-Pr₂O were added. The solution crystallized overnight at 4° C. The crystals were collected by filtration and washed with i-Pr₂O to yield 4.3 g of pure product (51%).

Example 19

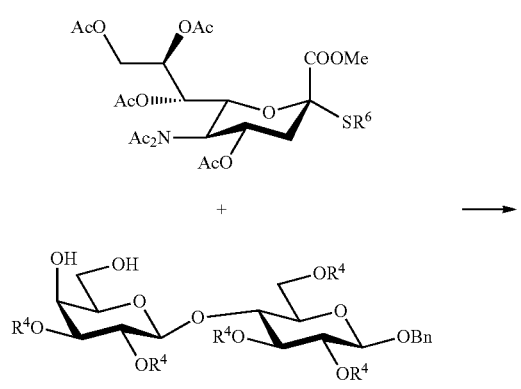

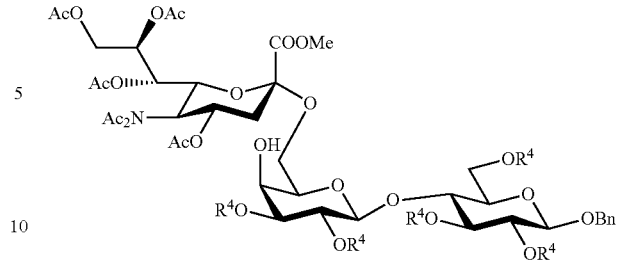

R⁶: ethyl, isopropyl, t-butyl, cyclohexyl, benzyl
R⁴: pivaloyl, benzoyl

General procedure: To a −20° C. cooled solution of donor (1.4 eq.) and acceptor (10.5 mmol) in DCM/THF mixture (75 mL+15 mL) NBS (1.6 eq.) was added followed by TfOH (0.42 eq.). The reaction mixture was stirred for 30 min at this temperature. An aq. solution of 7.5% Na₂S₂O₃ in saturated aq. NaHCO₃ (45 mL) was added to quench, and the biphasic mixture was stirred for 20 min, the phases were separated and the organic one was washed once with water. The product was taken into the acidic deprotection step without further purification.

R⁴: benzoyl $^1$H NMR (CDCl₃) δ (ppm): 1.85 (s, 3H); 1.9 (s, 3H); 2-2.2 (m, 13H); 2.48 (dd, 1H; J=4.8 Hz, J=12.9 Hz); 3.07 (m, 1H); 3.2 (m, 1H); 3.35 (m, 1H); 3.65 (m, 1H); 3.8 (m, 4H); 4.1 (m, 1H); 4.2-4.4 (m, 3H); 4.4-4.6 (m, 3H); 4.65-4.9 (m, 4H); 5.05 (m, 1H); 5.15 (M, 1H); 5.25 (m, 1H); 5.7 (m, 12H); 7-7.6 (m, 20H); 7.8-8.1 (m, 10H).

$^{13}$C NMR (CDCl₃) δ (ppm): 20.7, 20.8, 20.9, 21.0, 25.8, 27.4, 38.4, 52.7, 56.4, 62.2, 65.1 (2C), 67.0, 68.1, 68.8, 70.1, 70.2, 72.0, 72.3, 72.6, 73.1, 73.3, 74.3, 97.8, 98.5, 101.5, 127.6, 129.6, 132.8-133.4, 136.5, 164.9, 165.2 (2C), 165.6, 166.6, 169.4, 170.3, 170.8, 171.4, 173.4, 174.6.

R⁴: pivaloyl $^1$H NMR (CDCl₃) δ (ppm): 1.05-1.3 (m, 15H); 1.75 (dd, 1H, J=10.9 Hz, J=12.9 Hz); 1.95, 2.0, 2.05, 2.15, 2.25 (5s, 18H); 2.64 (dd, 1H, J=5.5 Hz, 12.9 Hz); 3.18 (m, 1H); 3.35 (m, 1H); 3.53 (m, 1H); 3.75 (m, 1H); 3.85 (s, 3H); 4.15-4.25 (m, 4H); 4.35-4.45 (m, 2H); 4.45-4.65 (m, 5H); 4.8 (m, 1H); 4.95 (dd, 1H, J=7.9 Hz, J=9.7 Hz); 5.05 (m, 1H); 5.1-5.3 (m, 5H); 5.7 (m, 1H); 7.5 (m, 5H).

$^{13}$C NMR (CDCl₃) δ (ppm): 20.99, 21.14, 21.19, 21.23, 27.29, 27.40, 27.42, 38.76, 38.89, 38.90, 39.06, 39.12, 53.04, 54.67, 57.00, 60.39, 62.25, 65.66, 66.97, 68.86, 69.59, 69.82, 70.45, 71.69, 72.00, 72.61, 72.77, 73.40, 73.65, 98.30, 99.25, 100.25, 128.11, 128.16, 128.53, 136.82, 166.92, 169.71, 170.56, 170.80, 171.41, 173.72, 174.71, 176.42, 177.00, 177.12, 179.91.

Example 20

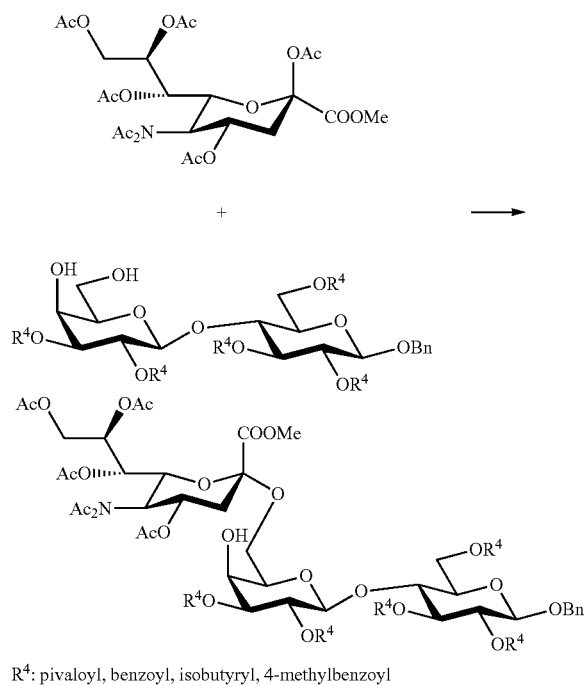

R⁴: pivaloyl, benzoyl, isobutyryl, 4-methylbenzoyl

To a 4° C. cooled solution of donor (10 g, 17.4 mmol) and acceptor (1.4 eq) in DCM (100 mL) BF$_3$.OEt$_2$ (1.6 mL, 0.75 eq) was added and the reaction stirred at this temperature for 16 h. The reaction was quenched with NaHCO$_3$ and the biphasic mixture was stirred for 10 min. The organic phase was washed with water and evaporated in vacuo. The residue was taken without further purification into the acidic deprotection step.

R⁴: 4-methylbenzoyl $^1$H NMR (CDCl$_3$) δ (ppm): 1.85 (s, 3H); 1.9 (s, 3H); 2-2.2 (m, 13H); 2.25-2.44 (m, 15H); 2.48 (dd, 1H; J=4.8 Hz, J=12.9 Hz); 3.07 (m, 1H); 3.2 (m, 1H); 3.35 (m, 1H); 3.65 (m, 1H); 3.8 (m, 4H); 4.1 (m, 1H); 4.2-4.4 (m, 3H); 4.4-4.6 (m, 3H); 4.65-4.9 (m, 4H); 5.05 (m, 1H); 5.15 (M, 1H); 5.25 (m, 1H); 5.7 (m, 12H); 6.9 (m, 2H); 7-7.25 (m, 13H); 7.7-7.9 (m, 10H).

$^{13}$C NMR (CDCl$_3$) δ (ppm): 20.7, 20.8, 20.9, 21.0, 21.14, 21.27, 21.62, 21.66, 25.8, 27.4, 38.4, 52.7, 56.4, 62.2, 65.1 (2C), 67.0, 68.1, 68.8, 70.1, 70.2, 72.0, 72.3, 72.6, 73.1, 73.3, 74.3, 97.8, 98.5, 101.5, 127.6, 129.6, 132.8-133.4, 136.5, 164.9, 165.2 (2C), 165.6, 166.6, 169.4, 170.3, 170.8, 171.4, 173.4, 174.6.

R⁴: isobutyryl $^1$H NMR (CDCl$_3$) δ (ppm): 1.0 (m, 30H), 1.6 (dd, 1H, J=1.8 Hz, J=2.05 Hz); 1.80, 1.87, 1.90, 1.97 (4s, 12H); 2.12 (2s, 6H); 2.2-2.6 (m, 6H); 3.15 (m, 1H); 3.25 (m, 1H); 3.4 (m, 1H); 3.55-3.8 (m, 6H); 3.95-4.3 (m, 4H); 4.3-4.55 (m, 5H); 4.67 (d, 1H, J=12 Hz); 4.75-5.2 (m, 7H); 7.1 (m, 5H).

$^{13}$C NMR (CDCl$_3$) δ (ppm): 18.59, 18.80, 18.86, 18.94, 19.07, 19.12, 19.28, 19.29, 19.32, 20.84, 20.98, 20.99, 21.11, 25.95, 27.98, 33.96, 34.03, 34.07, 50.28, 52.29, 54.67, 56.79, 60.16, 61.93, 62.21, 65.51, 68.73, 69.23, 69.63, 70.51, 71.49, 72.33, 72.39, 72.82, 73.17, 73.23, 75.74, 98.19, 99.10, 101.12, 127.92, 128.04, 128.47, 136.79, 166.78, 169.64, 170.42, 170.75, 171.49, 173.66, 174.83, 175.32, 175.54, 175.64, 175.70, 176.49.

Example 21

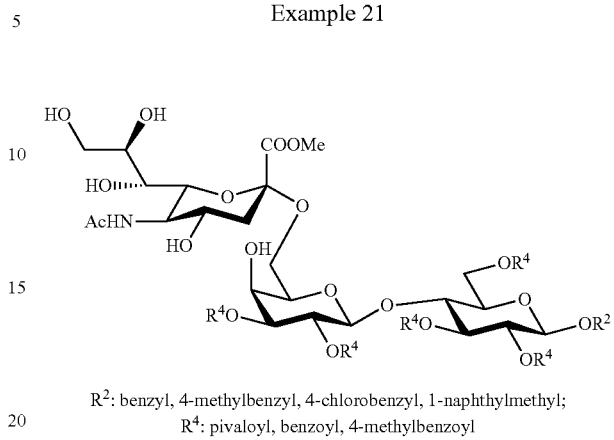

R²: benzyl, 4-methylbenzyl, 4-chlorobenzyl, 1-naphthylmethyl;
R⁴: pivaloyl, benzoyl, 4-methylbenzoyl The syrup obtained in examples 19 or 20 was diluted with MeOH, cooled to 5° C. and sulfuric acid was added dropwise. The reaction mixture was stirred for 48 h at this temperature and neutralized with Et$_3$N. MeOH was evaporated and the residue was dissolved in EtOAc, washed with water once and with 5/1 water brine. The organic phase was evaporated in vacuo and the residue was crystallized (yield: 50-60% for two steps).

R²: benzyl, R⁴: benzoyl $^1$H(CD$_3$OD) δ (ppm): 1.5 (dd, 1H, J=11.7 Hz, J=12.6 Hz); 2.0 (s, 3H); 2.45 (dd, 1H, J=4.6 Hz, J=12.8 Hz); 3.2 (m, 1H); 3.4-3.7 (m, 7H); 3.7-3.85 (m, 5H); 3.95 (m, 1H); 4.1 (d, 1H, J=3.5 Hz); 4.25 (dd, 1H, J=9.2 Hz, J=9.5 Hz); 4.45-4.65 (m, 3H); 4.75 (d, 1H, J=12.2 Hz); 5.15 (dd, 1H, J=3.3 Hz, J=10.4 Hz); 5.35 (dd, 1H, J=8 Hz, J=9.7 Hz); 5.64 (dd, 1H, J=7.9 Hz, J=10.3 Hz); 5.69 (dd, 1H, J=9.2 Hz, J=9.4 Hz); 7.05-7.65 (m, 20H), 7.8-8.1 (m, 10H).

$^{13}$C(CD$_3$OD) δ (ppm): 21.62, 39.03, 52.37, 52.44, 60.04, 63.14, 65.25, 67.44, 68.41, 70.50, 70.87, 72.58, 73.24, 73.39, 73.66, 73.97, 74.79, 77.15, 127.73, 128.16, 128.27, 128.37, 128.63, 129.08, 129.41, 129.46, 129.49, 129.54, 129.59, 129.72, 129.81, 129.89, 133.18, 137.18, 165.63, 165.66, 165.95, 166.01, 166.22, 169.35, 173.99.

R²: benzyl, R⁴: pivaloyl $^1$H NMR (CDCl$_3$) δ (ppm): 1.0-1.3 (m, 45H); 1.9 (t, J=12.2 Hz); 2.05 (s, 3H); 2.72 (m, 2H); 3.15 (m, 1H); 3.45 (m, 1H); 3.55 (m, 3H); 3.7-3.9 (m, 10H); 4.02 (m, 1H); 4.22 (dd, 1H, J=5.5 Hz, J=11.5 Hz); 4.4-4.6 (m, 4H); 4.72-4.85 (m, 3H); 4.95 (dd, 1H, J=7.9 Hz, J=9.6 Hz); 5.13 (dd, 1H, J=7.9 Hz, J=10.3 Hz); 5.18 (t, 1H, 9.4 Hz); 6.65 (d, 1H, J=6.5 Hz); 7.2-7.35 (m, 5H).

$^{13}$C(CDCl$_3$) δ (ppm): 23.22, 27.23, 27.29, 27.37, 27.37, 27.44, 27.52, 27.59, 31.20, 38.94, 39.07, 39.12, 53.18, 53.65, 62.32, 63.68, 66.12, 67.77, 68.72, 69.41, 69.95, 70.92, 71.70, 71.79, 73.44, 73.70, 74.03, 99.13, 99.64, 99.83, 128.74, 129.32, 133.90, 135.38, 169.61, 174.25, 176.64, 177.19, 177.57, 177.87, 178.21.

R²: benzyl, R⁴: 4-methylbenzoyl $^1$H(CD$_3$OD) δ (ppm): 1.5 (dd, 1H, J=11.7 Hz, J=12.6 Hz); 2.0 (s, 3H); 2.25 (s, 3H); 2.31-2.43 (m, 12H); 2.48 (dd, 1H, J=4.6 Hz, J=12.8 Hz); 3.2 (m, 1H); 3.4-3.7 (m, 7H); 3.7-3.85 (m, 5H); 3.90 (m, 1H); 4.1 (d, 1H, J=3.5 Hz); 4.24 (dd, 1H, J=9.2 Hz, J=9.5 Hz); 4.44-4.64 (m, 3H); 4.73 (d, 1H, J=12.2 Hz); 5.12 (dd, 1H, J=3.2 Hz, J=10.4 Hz); 5.32 (dd, 1H, J=8 Hz, J=9.6 Hz); 5.57-5.70 (m, 2H); 6.87 (m, 2H); 7.05-7.3 (m, 13H); 7.65-7.95 (m, 10H).

$^{13}$C(CD$_3$OD) δ (ppm): 21.05, 21.14, 21.27, 21.62, 21.66, 39.03, 52.37, 52.44, 60.04, 63.14, 65.25, 67.44, 68.41, 70.50, 70.87, 72.58, 73.24, 73.39, 73.66, 73.97, 74.79, 77.15, 127.73, 128.16, 128.27, 128.37, 128.63, 129.08, 129.41, 129.46, 129.49, 129.54, 129.59, 129.72, 129.81, 129.89, 133.18, 137.18, 165.63, 165.66, 165.95, 166.01, 166.22, 169.35, 173.99.

$R^2$: 4-chlorobenzyl, $R^4$: pivaloyl $^1$H NMR (CDCl$_3$) δ (ppm): 1.0-1.3 (m, 45H); 1.9 (t, J=12 Hz); 2.05 (s, 3H); 2.64 (d, 1H, J=5.4); 2.75 (dd, 1H, J=3.7 Hz, J=12.5 Hz); 2.9 (m, 1H); 3.3 (m, 1H); 3.45 (m, 1H); 3.55 (m, 2H); 3.65-3.95 (m, 10H); 4.02 (m, 1H); 4.21 (dd, 1H, J=5.3 Hz, J=11.7 Hz); 4.4-4.6 (m, 4H); 4.67-4.85 (m, 2H); 4.95 (dd, 1H, J=8.3 Hz, J=9.4 Hz); 5.15 (m, 2H); 6.48 (d, 1H, J=7.5 Hz); 7.18 (m, 2H); 7.28 (m, 2H).

$^{13}$C(CDCl$_3$) δ (ppm): 23.22, 27.28, 27.30, 27.37, 27.43, 27.52, 27.58, 31.19, 38.93, 39.07, 39.12, 53.18, 53.65, 62.32, 63.66, 66.15, 67.81, 68.77, 69.50, 70.02, 70.99, 71.67, 71.81, 73.45, 73.59, 73.98, 99.09, 99.69, 100.01, 128.53, 129.11, 133.75, 135.19, 169.54, 174.21, 176.59, 177.08, 177.42, 177.57, 178.17.

$R^2$: 1-naphthylmethyl, $R^4$: pivaloyl $^1$H NMR (CDCl$_3$) δ (ppm): 1.0-1.4 (m, 45H); 1.85 (t, J=12.2 Hz); 2.05 (s, 3H); 2.69 (dd, 1H, J=3.7 Hz, J=12.5 Hz); 2.8 (m, 1H); 3.45 (m, 1H, 3.55 (m, 3H); 3.7-3.95 (m, 10H); 4.05 (m, 1H); 4.22 (dd, 1H, J=5.6 Hz, J=11.8 Hz); 4.44 (d, 1H, J=7.8 Hz); 4.54 (m, 1H); 4.61 (d, 1H, J=7.9 Hz); 4.78 (dd, 1H, J=3.2 Hz, J=10.4 Hz); 4.95 (m, 2H); 5.12 (m, 2H); 5.3 (d, 1H, 11.7 Hz); 7.35-7.5 (m, 4H); 7.8 (m, 2H); 8.0 (m, 1H).

$^{13}$C(CDCl$_3$) δ (ppm): 22.96, 27.12, 27.27, 27.32, 27.37, 27.47, 31.15, 38.75, 38.83, 38.87, 39.00, 39.12, 53.62, 54.67, 55.07, 61.43, 62.27, 63.77, 65.94, 66.81, 68.61, 68.99, 69.41, 70.94, 71.65, 71.91, 73.32, 73.52, 74.31 99.25, 99.36, 99.93, 123.92, 125.31, 126.04, 126.62, 127.06, 128.72, 129.16, 131.80, 132.26, 132.26, 133.77, 169.77, 174.51, 176.41, 176.91, 177.38, 177.76, 178.07.

$R^2$: 4-methylbenzyl, $R^4$: pivaloyl $^1$H NMR (CDCl$_3$) δ (ppm): 1.0-1.3 (m, 45H); 1.9 (t, J=12.3 Hz); 2.05 (s, 3H); 2.25 (s, 3H); 2.65 (m, 1H); 2.83, (m, 1H); 3.35 (m, 1H); 3.45 (m, 1H); 3.55 (m, 3H); 3.6-3.85 (m, 12H); 3.95 (m, 1H); 4.15 (m, 1H); 4.32-4.5 (m, 3H); 4.63-4.8 (m, 2H); 4.85 (dd, 1H, J=8 Hz, J=9.4 Hz); 5.08-5.15 (m, 2H); 7.05 (m, 5H).

$^{13}$C(CDCl$_3$) δ (ppm): 21.10, 22.93, 27.02, 27.03, 27.09, 27.17, 38.64, 38.78, 38.84, 53.36, 54.89, 61.33, 62.32, 63.34, 65.87, 67.38, 68.38, 68.60, 69.16, 70.18, 70.65, 71.44, 71.69, 73.18, 73.33, 73.77, 98.71, 98.88, 99.63, 128.12, 128.99, 133.23, 137.75, 169.33, 173.98, 176.32, 176.98, 177.28, 177.56, 177.95.

Example 22

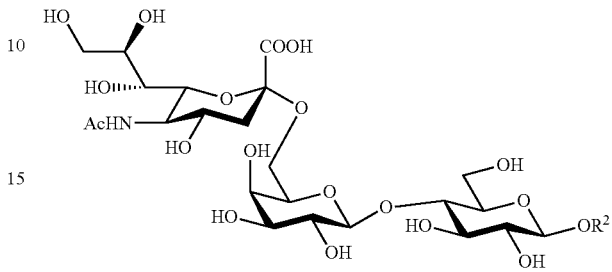

Method A: To a solution of a protected or partially protected trisaccharide according to any of the examples 16-21 in 5 volumes of MeOH, 1M aqueous solution of NaOH was added slowly. The reaction mixture stirred overnight at RT and Amberlite IR 120 H$^+$ was added to neutralize the base. The mixture was filtered and the solvent was evaporated in vacuo. The material was then dissolved in MeOH and EtOH, and TBME was added slowly. The precipitate was filtered off and washed twice with TBME. The white solid obtained was dissolved in 1M NaOH and the reaction mixture was stirred for 6 h. IR-120 H$^+$ was used to neutralize the base and the solvent was evaporated in vacuo. After coevaporation with EtOH (twice) the product was dissolved in MeOH and i-PrOH was added slowly to give a solid in free acid form.

Method B: To a solution of a protected or partially protected trisaccharide according to any of the examples 16-21 in MeOH NaOMe was added and the reaction mixture was stirred for 5 h at 45° C. The cooled solution was washed with heptane and acetone was added. The precipitate was filtered off and dissolved in 1M NaOH and the reaction mixture was stirred for 6 h. IR-120 H$^+$ was used to neutralize the base and the solvent was evaporated in vacuo. After coevaporation with EtOH (twice) the product was dissolved in MeOH and i-PrOH was added slowly to give a solid in free acid form.

$R^2$: benzyl $^1$H(CD$_3$OD) δ (ppm): 1.63 (t, 1H, J=11.9 Hz); 2.00 (s, 3H); 2.78 (dd, 1H, J=4.5 Hz, J=12.2 Hz); 3.28-3.49 (m, 4H); 3.50-3.79 (m, 9H); 3.80-3.97 (m, 5H); 4.02 (dd, 1H, J=7.5 Hz, J=10 Hz); 4.35 (m, 1H); 4.42 (d, 1H, J=7.8 Hz); 4.66 (d, 1H, J=11.7 Hz); 7.22-7.37 (m, 3H); 7.38-7.46 (m, 2H).

$^{13}$C(CD$_3$OD) δ (ppm): 21.55, 41.26, 52.70, 60.81, 63.21, 63.42, 68.56, 69.01, 69.30, 70.66, 71.15, 72.12, 73.08, 73.55, 73.78, 74.47, 75.28, 75.32, 80.03, 100.29, 101.89, 103.36, 127.36, 127.87, 128.01, 128.12, 137.72, 173.36, 173.88.

$R^2$:4-chlorobenzyl $^1$H(CD$_3$OD) δ (ppm): 1.62 (t, 1H, J=12 Hz); 2.00 (s, 3H); 2.77 (dd, 1H, J=4.7 Hz, J=12.1 Hz); 3.28-3.49 (m, 4H); 3.50-3.79 (m, 9H); 3.80-3.97 (m, 5H); 4.02 (dd, 1H, J=7.5 Hz, J=10 Hz); 4.35 (m, 1H); 4.42 (d, 1H, J=7.8 Hz); 4.66 (d, 1H, J=11.7 Hz); 7.24 (m, 2H); 7.32 (m, 2H).

$^{13}$C(CD$_3$OD) δ (ppm): 21.52, 41.23, 52.72, 60.79, 63.23, 63.42, 68.61, 69.03, 69.31, 70.56, 71.14, 72.13, 73.11, 73.56, 73.79, 74.48, 75.23, 75.31, 80.09, 100.17, 101.91, 103.21, 127.36, 127.89, 133.01, 136.76, 173.29, 173.78.

R²: 1-naphthylmethyl

¹H(CD₃OD) δ (ppm): 1.62 (t, 1H, J=11.8 Hz); 2.00 (s, 3H); 2.78 (dd, 1H, J=4.5 Hz, J=12.2 Hz); 3.28-3.49 (m, 4H); 3.50-3.79 (m, 9H); 3.80-3.97 (m, 5H); 4.02 (dd, 1H, J=7.6 Hz, J=10.1 Hz); 4.35 (m, 1H); 4.42 (d, 1H, J=7.8 Hz); 4.68 (d, 1H, J=11.8 Hz); 7.32-7.54 (m, 4H); 7.7 (m, 2H); 7.95 (m, 1H).

¹³C(CD₃OD) δ (ppm): 21.54, 41.28, 52.72, 60.81, 63.20, 63.44, 68.53, 69.06, 69.38, 70.64, 71.12, 72.14, 73.05, 73.54, 73.65, 74.45, 75.24, 75.33, 80.02, 100.25, 101.87, 103.21, 122.91, 124.82, 125.25, 125.93, 127.06, 128.72, 129.16, 132.80, 133.12, 135.97, 136.88, 173.36, 173.88.

R²: 4-methylbenzyl

¹H(CD₃OD) δ (ppm): 1.63 (t, 1H, J=11.9 Hz); 2.00 (s, 3H); 2.32 (s, 3H); 2.78 (dd, 1H, J=4.5 Hz, J=12.2 Hz); 3.28-3.49 (m, 4H); 3.50-3.79 (m, 9H); 3.80-3.97 (m, 5H); 4.02 (dd, 1H, J=7.5 Hz, J=10 Hz); 4.35 (m, 1H); 4.42 (d, 1H, J=7.8 Hz); 4.66 (d, 1H, J=11.7 Hz); 7.21 (m, 4H).

¹³C(CD₃OD) δ (ppm): 20.02, 21.55, 41.26, 52.70, 60.81, 63.21, 63.42, 68.56, 69.01, 69.30, 70.66, 71.15, 72.12, 73.08, 73.55, 73.78, 74.47, 75.28, 75.32, 80.03, 99.98, 100.89, 102.36, 127.36, 127.87, 128.01, 128.12, 133.26, 137.72, 173.36, 173.88

Example 23

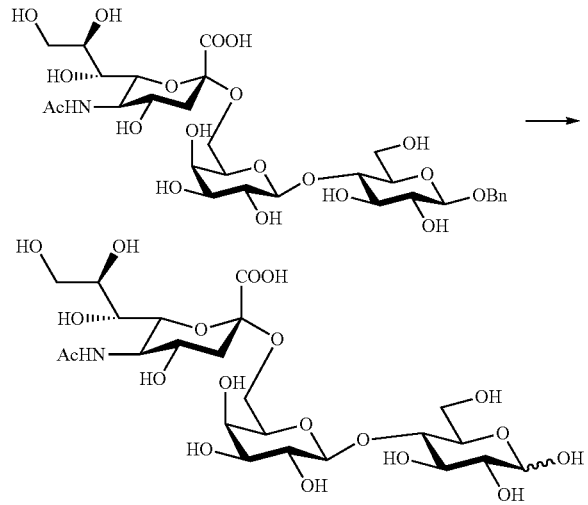

To a solution of 40 g of free acid in a mixture of methanol and water (250 mL+300 mL) 4 g of Pd/C (10%) were added. The reaction mixture was stirred 2 d at RT under H₂ pressure (balloon). The mixture was then filtered through a pad of Celite and the solvent was evaporated in vacuo. The residue was dissolved in 80 mL of H₂O and dropped to 1200 mL of EtOH. The slurry was filtrated, the solid was washed with EtOH, acetone and a mixture of 1/1 acetone/Et₂O. The solid was dried to give 35 g of 6'-O-sialyllactose.

¹H (D₂O) (anomeric mixture of glucose 0.6/0.4 β/α): 1.75 (dd, 1H, J=12.0 Hz, J=11.9 Hz); 2.05 (s, 3H); 2.7 (dd, 1H, J=12.0 Hz, J=4.6 Hz); 3.31 (dd, 0.6H, J=7.8 Hz, J=8.9 Hz); 3.5-3.75 (m, 11.4H); 3.76-4.05 (m, 8.9H); 4.43 (d, 1H, J=7.8 Hz); 4.67 (d, 0.6H, J=7.8 Hz); 5.23 (d, 0.4H, J=3.8 Hz).

¹³C, 19.51, 24.78, 42.82, 54.51, 60.15, 62.83, 62.99, 65.36, 66.3, 71.1, 71.24, 72.68, 73.51, 73.78, 74.35, 74.53, 75.09, 75.24, 76.42, 76.45, 77.35, 77.39, 82.35, 82.46, 94.54, 98.37, 103.01, 105.92, 105.95, 176.21, 177.64.

Example 24

Salt Formation

Inorganic and organic salts of 6'-SL or 6'-SL glycosides were obtained from acidic 6'-SL or 6'-SL glycosides. The pH of the acid in alcohol or alcohol/water was adjusted to 8.5-11 with an organic base selected from ethanolamine, diethylamine, tris-(hydroxymethyl)-methyl amine base and choline hydroxide or with an inorganic base selected from metal hydroxide, carbonate and bicarbonate. The mixture was then diluted with alcohol and concentrated in vacuo. The slurry obtained was then filtered and washed with alcohol.

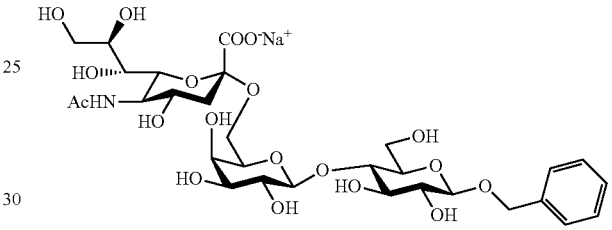

¹H(CD₃OD) δ (ppm): 1.63 (t, 1H, J=11.9 Hz); 2.02 (s, 3H); 2.82 (m, 1H); 3.33-3.45 (m, 4H); 3.46-3.61 (m, 5H); 3.62-3.97 (m, 12H); 4.02 (dd, 1H, J=7.5 Hz, J=10 Hz); 4.37 (m, 2H); 4.66 (d, 1H, J=11.9 Hz); 7.31 (m, 3H); 7.41 (m, 2H).

¹³C(CD₃OD) δ (ppm): 21.10, 40.60, 52.04, 60.22, 62.78, 67.90, 68.51, 68.69, 70.11, 70.61, 70.64, 71.44, 72.44, 72.83, 73.17, 73.92, 74.50, 74.70, 79.82, 99.76, 101.23, 103.52, 127.00, 127.44, 127.56, 137.21, 172.68, 173.28.

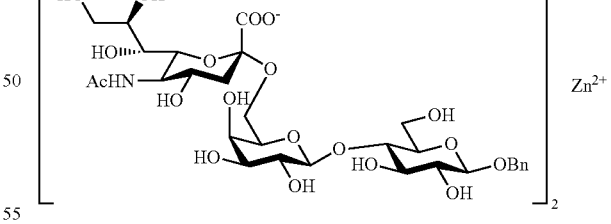

¹H(CD₃OD) δ (ppm): 1.71 (t, 1H, J=11.1 Hz); 2.00 (s, 3H); 2.78 (dd, 1H, J=4.5 Hz, J=12.2 Hz); 3.28-3.49 (m, 4H); 3.50-3.79 (m, 9H); 3.80-3.97 (m, 5H); 4.02 (dd, 1H, J=7.5 Hz, J=10 Hz); 4.35 (m, 1H); 4.42 (d, 1H, J=7.8 Hz); 4.66 (d, 1H, J=11.7 Hz); 7.22-7.37 (m, 3H); 7.38-7.46 (m, 2H).

¹³C(CD₃OD) δ (ppm): 21.77, 41.09, 52.78, 60.87, 61.32, 63.06, 63.64, 63.21, 68.26, 69.11, 70.67, 71.22, 71.36, 72.01, 73.00, 73.37, 73.58, 73.66, 74.39, 75.19, 75.32, 75.87, 79.40, 80.35, 99.92, 101.86, 101.94, 103.86, 104.00, 127.55, 127.99, 128.13, 137.83, 174.03, 174.08

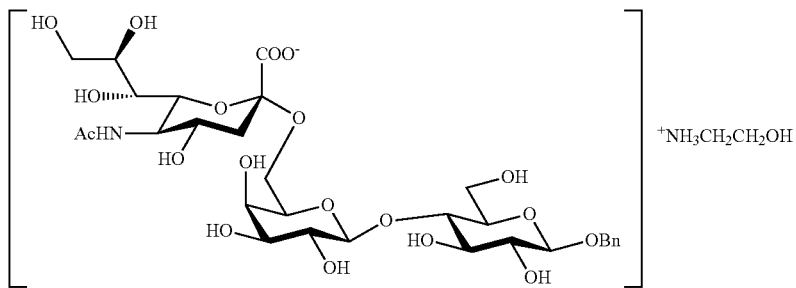
¹H (CD₃OD) δ (ppm): 1.63 (dd, 1H, J=11.7 Hz, J=12.2 Hz); 2.00 (s, 3H); 2.78 (dd, 1H, J=4.5 Hz, J=12.2 Hz); 2.92 (m, 4H); 3.33-3.47 (m, 2H); 3.46-3.57 (m, 5H); 3.58-3.78 (m, 9H); 3.78-3.90 (m, 5H); 3.93 (dd, 1H, J=2.5, J=11.7 Hz); 4.02 (dd, 1H, J=7.5 Hz, J=10 Hz); 4.35 (m, 1H); 4.42 (d, 1H, J=7.8 Hz); 4.66 (d, 1H, J=11.7 Hz); 7.22-7.37 (m, 3H); 7.38-7.46 (m, 2H).
¹³C(CD₃OD) δ (ppm): 21.55, 41.26, 44.83, 52.70, 58.85, 60.81, 63.21, 63.42, 68.56, 69.01, 69.30, 70.66, 71.15, 72.12, 73.08, 73.55, 73.78, 74.47, 75.28, 75.32, 80.03, 99.98, 100.89, 102.36, 127.36, 127.87, 128.01, 128.12, 137.72, 173.36, 173.88
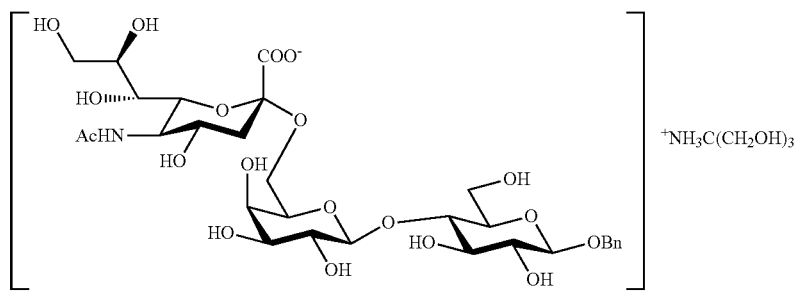
¹H (CD₃OD) δ (ppm): 1.63 (dd, 1H, J=11.9 Hz, J=12.1 Hz); 2.00 (s, 3H); 2.78 (dd, 1H, J=4.5 Hz, J=12.2 Hz); 3.33-3.48 (m, 2H); 3.48-3.79 (m, 19H); 3.93 (dd, 1H, J=2.5, J=11.8 Hz); 4.02 (dd, 1H, J=7.5 Hz, J=10 Hz); 4.35 (m, 1H); 4.42 (d, 1H, J=7.8 Hz); 4.66 (d, 1H, J=11.7 Hz); 7.22-7.37 (m, 3H); 7.38-7.46 (m, 2H).
¹³C(CD₃OD) δ (ppm): 21.60, 41.22, 52.71, 59.62, 60.89, 61.38, 63.23, 63.39, 68.64, 68.97, 69.25, 70.64, 71.26, 73.68, 75.24, 75.27, 80.16, 100.39, 101.87, 103.94, 127.52, 127.97, 128.00, 128.11, 137.85, 173.40, 173.90
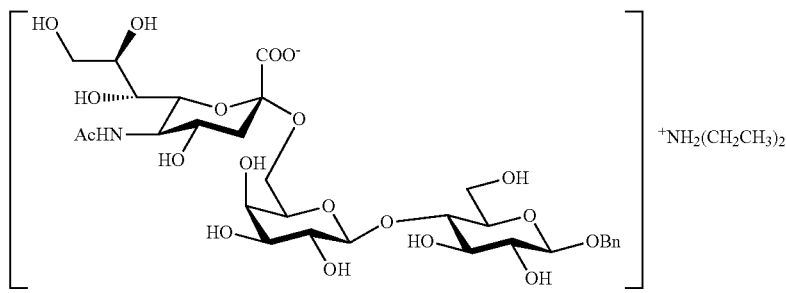

¹H (CD₃OD) δ (ppm): 1.28 (t, 6H, J=11.8 Hz); 1.65 (dd, 1H, J=11.9 Hz, J=12.1 Hz); 2.00 (s, 3H); 2.79 (dd, 1H, J=4.5 Hz, J=12.2 Hz); 3.00 (q, 4H); 3.33-3.57 (m, 7H); 3.57-3.77 (m, 5H); 3.78-3.89 (m, 4H); 3.93 (dd, 1H, J=11.9 Hz, J=2.4 Hz); 4.00 (dd, 1H, J=7.1 Hz, J=9.7 Hz); 4.35 (m, 1H); 4.42 (d, 1H, J=7.8 Hz); 4.66 (d, 1H, J=11.8 Hz); 7.22-7.37 (m, 3H); 7.38-7.46 (m, 2H).

¹³C(CD₃OD) δ (ppm): 10.64, 21.57, 41.29, 42.29, 52.74, 60.89, 63.23, 63.43, 68.63, 68.95, 69.30, 70.62, 71.25, 72.04, 73.06, 73.41, 73.73, 74.47, 75.26, 75.28, 80.15, 100.41, 101.90, 103.95, 127.51, 127.97, 127.99, 128.10, 137.88, 173.35, 173.85

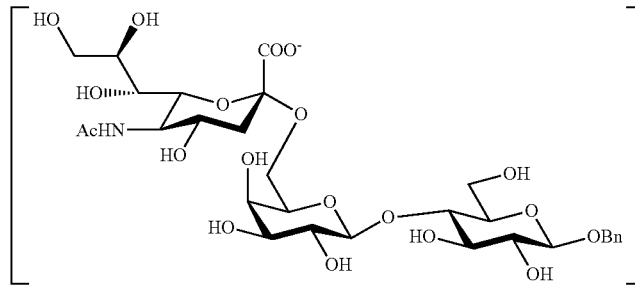
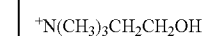

¹H (CD₃OD) δ (ppm): 1.63 (dd, 1H, J=11.9 Hz, J=12.1 Hz); 1.98 (s, 3H); 2.80 (dd, 1H, J=4.5 Hz, J=12.2 Hz); 3.19 (s, 9H); 3.33-3.56 (m, 8H); 3.56-3.77 (m, 7H); 3.78-3.94 (m, 5H); 3.95-4.04 (m, 4H); 4.34 (m, 1H); 4.39 (d, 1H, J=7.8 Hz); 4.66 (d, 1H, J=11.8 Hz); 7.22-7.36 (m, 3H); 7.40 (m, 2H).

¹³C(CD₃OD) δ (ppm): 21.56, 40.95, 41.34, 52.75, 53.48, 53.53, 53.59, 55.92, 60.96, 63.15, 63.50, 63.84, 67.85, 68.65, 68.90, 69.31, 69.47, 70.61, 71.28, 72.05, 73.05, 73.41, 73.72, 74.45, 75.29, 76.89, 80.17, 100.42, 101.92, 103.97, 109.98, 127.52, 127.97, 128.11, 137.90, 138.29, 173.26, 173.85

6'-SL Na⁺ Salt

¹H (D₂O) δ (ppm): 1.54 (t, 1H, J=12.1 Hz); 1.82 (s, 3H); 2.52 (dd, 1H, J=4.8 Hz, J=12.3 Hz); 3.10 (m, 1H); 3.27-3.55 (m, 10H); 3.56-3.82 (m, 9H); 4.23 (d, 1H, J=7.8 Hz); 4.48 (d, 0.7H, J=8 Hz); 5.03 (d, 0.3H, J=3.7 Hz).

¹³C (D₂O) δ (ppm): 22.17, 40.19, 51.87, 52.10, 60.38, 62.71, 63.68, 68.46, 68.61, 70.87, 71.90, 72.44, 72.60, 73.78, 74.04, 74.68, 74.76, 79.80, 79.86, 96.16, 100.36, 103.33, 173.62, 174.99.

6'-SL Zn² Salt

¹H (D₂O) δ (ppm): 1.54 (t, 1H, J=12.1 Hz); 1.82 (s, 3H); 2.52 (dd, 1H, J=4.8 Hz, J=12.3 Hz); 3.10 (m, 1H); 3.27-3.55 (m, 10H); 3.56-3.82 (m, 9H); 4.23 (d, 1H, J=7.8 Hz); 4.48 (d, 0.7H, J=8 Hz); 5.03 (d, 0.3H, J=3.7 Hz).

¹³C (D₂O) δ (ppm): 22.16, 40.16, 51.87, 60.15, 60.31, 62.69, 63.67, 68.45, 68.60, 70.02, 70.86, 71.12, 71.72, 71.88, 72.43, 72.59, 73.77, 74.71, 74.73, 79.69, 91.90, 95.72, 100.34, 103.31, 173.63, 174.99.

6'-SL Ethanolammonium Salt

¹H (D₂O) δ (ppm): 1.54 (t, 1H, J=12.1 Hz); 1.82 (s, 3H); 2.52 (dd, 1H, J=4.8 Hz, J=12.3 Hz); 2.92 (m, 2H); 3.10 (m, 1H); 3.27-3.55 (m, 10H); 3.56-3.82 (m, 11H); 4.23 (d, 1H, J=7.8 Hz); 4.48 (d, 0.7H, J=8 Hz); 5.03 (d, 0.3H, J=3.7 Hz).

¹³C (D₂O) δ (ppm): 22.16, 40.19, 41.37, 51.87, 52.09, 57.93, 60.32, 62.70, 63.67, 68.46, 68.62, 70.03, 70.87, 71.13, 71.91, 72.43, 72.60, 73.80, 74.71, 74.74, 79.69, 79.80, 95.73, 100.35, 103.32, 173.61, 174.98.

6'-SL tris-(hydroxymethyl)-methyl ammonium salt

¹H (D₂O) δ (ppm): 1.54 (t, 1H, J=12.1 Hz); 1.82 (s, 3H); 2.52 (dd, 1H, J=4.8 Hz, J=12.3 Hz); 3.10 (m, 1H); 3.56-3.82 (m, 9H); 4.24 (d, 1H, J=7.8 Hz); 4.47 (d, 0.7H, J=8 Hz); 5.02 (d, 0.3H, J=3.7 Hz).

¹³C (D₂O) δ (ppm): 22.15, 40.19, 51.87, 59.90, 60.83, 62.70, 63.67, 68.46, 68.61, 70.03, 70.87, 71.13, 71.72, 71.90, 72.43, 72.60, 73.79, 74.71, 74.74, 79.70, 79.81, 95.73, 100.35, 103.32, 173.60, 174.98.

6'-SL Diethyl Ammonium Salt

¹H (D₂O) δ (ppm): 1.05 (t, 6H, J=7.3 Hz); 1.54 (t, 1H, J=12.1 Hz); 1.82 (s, 3H); 2.52 (dd, 1H, J=4.8 Hz, J=12.3 Hz); 2.84 (q, 4H, J=7.3 Hz); 3.10 (m, 1H); 3.27-3.55 (m, 10H); 3.56-3.82 (m, 9H); 4.23 (d, 1H, J=7.8 Hz); 4.48 (d, 0.7H, J=8 Hz); 5.03 (d, 0.3H, J=3.7 Hz).

¹³C (D₂O) δ (ppm): 10.67, 22.13, 40.18, 42.35, 51.85, 52.09, 60.15, 60.31, 62.68, 63.67, 68.45, 68.58, 70.01, 70.84, 71.71, 71.88, 72.41, 72.58, 73.78, 74.72, 79.69, 79.80, 91.89, 95.72, 100.33, 103.31, 173.59, 174.95.

6'-SL Choline Salt

¹H (D₂O) δ (ppm): 1.54 (t, 1H, J=12.1 Hz); 1.82 (s, 3H); 2.52 (dd, 1H, J=4.8 Hz, J=12.3 Hz); 2.99, (s, 9H); 3.10 (m, 1H); 3.27-3.55 (m, 12H); 3.56-3.82 (m, 11H); 4.23 (d, 1H, J=7.8 Hz); 4.48 (d, 0.7H, J=8 Hz); 5.03 (d, 0.3H, J=3.7 Hz).

¹³C (D₂O) δ (ppm): 22.14, 40.17, 51.85, 52.10, 53.87, 53.92, 53.97, 55.67, 60.31, 62.69, 63.67, 67.42, 67.46, 67.50, 68.45, 68.58, 70.85, 71.11, 71.88, 72.41, 72.58, 73.77, 74.72, 79.68, 79.80, 91.89, 95.72, 100.33, 103.31, 173.59, 174.95.

Example 25

6'-SL K⁺ Salt 1 g of 6'-SL was dissolved in 3 mL of water and passed through a cationic ion-exchange column (Amberlite IRC50 K⁺ form). The fractions (2-7) were collected and lyophilized.

Example 26

6'-SL Ca²⁺ Salt 1 g of 6'-SL was dissolved in 3 mL of water and passed through a cationic ion exchange column (Amberlite IRC50 Ca²⁺ form). The fractions (2-7) were collected and lyophilized.

LIST OF REFERENCES 1. a) D. S, Newburg et al. *Annu. Rev. Nutr.* 2005, 25, 37-58 b) C. Kunz et al. *Acta Pædiatr.* 1993, 82, 903-912.
2. a) K. Furuhata et al. *Chem. Pharm. Bull.* 1986, 34, 2725-2731b) V. Pozsgay et al. *J. Carbohydr. Chem.* 1987, 6, 41-55 c) Y. Liu et al. *Chemistry & Biology* 2007, 14, 847-859 d) A. Rencurosi et al. *Carbohydr. Res.* 2002, 337, 473-483 e) WO 2010/116317 f) R. L. Thomas et al. *Tetrahedron Lett.* 1990, 31, 2825-2828 g) G. Pazynina et al. *Tetrahedron Lett.* 2002, 43, 8011-8013 h) K. Matsuoka et al. *Tetrahedron Lett.* 2004, 45, 9383-9386 i) EP-A-254105 j) EP-A-479769.
3. a) E. S. Simon et al. *JACS* 1988, 110, 7159-7163 b) E. S. Simon et al. *Methods in Enzymology* 1989, 179, 275-287 c) K. Ajisaka et al. *Carbohydr. Res.* 1994, 259, 103-115 d) H. Tanaka et al. *Biosci. Biotech. Biochem.* 1995, 59, 638-643 e) D. Schmidt et al. *Chem. Comm.* 2000, 1919-1920 f) I. Maru et al. *Biosci. Biotech. Biochem.* 1992, 56, 1557-1561.
4. a) US 2002/0064836 A1 b) US 2009/0082307 A1.
5. a) R. Kuhn et al. *Chem. Ber.* 1965, 98, 385-413 b) G. Grönberg et al. *Carbohydr. Res.* 1989, 191, 261-278 c) U.S. Pat. No. 6,288,222 d) U.S. Pat. No. 6,623,954.
6. a) K. Furuhata *Trends Glycosci. Glycotechnol.* 2004, 16, 143-169 b) D. K. Ress et al. *Curr. Org. Synth.* 2004, 1, 31-46 c) X. Chen et al. *ACS Chem. Biol.* 2010, 5, 163-176.
7. P. G. M. Wuts and T. W. Greene *Protective Groups in Organic Synthesis*, John Wiley & Sons, 2007

ABBREVIATIONS LIST

CMP-Neu5Ac cytidine 5'-monophospho-N-acetylneuraminic acid
DCM Dichloromethane
DMF N,N'-Dimethylformamide
DTPI 2,6-di-tert-butylpyridinium iodide
GlcNAc N-acetyl-glucosamine
HMOs Human Milk Oligosaccharides
6'-SL 6'-O-sialyllactose, Neu5Ac(α2-6)Gal(β1-4)Glc
NBS N-Bromosuccinimide
NeuAc Neuraminic acid
NIS N-Iodosuccinimide
RT Room temperature
THF tetrahydrofuran
TfOH Triflic acid
TMSOTf trimethylsilyl triflate
Tol toluene

The invention claimed is:

1. A method for the preparation of 6'-O-sialyllactose or a salt thereof, comprising the steps of:
   a) reaction of an acceptor of general formula 3

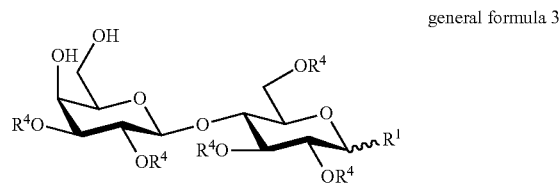

general formula 3 wherein $R^1$ is —$OR^2$, which $R^2$ is a group removable by catalytic hydrogenation
$R^4$ is selected from optionally substituted acyl provided that acetyl is excluded,
with a donor of general formula 4

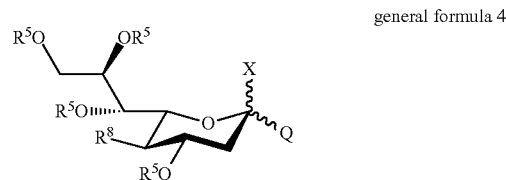

general formula 4 wherein $R^5$ is acetyl,
$R^8$ is selected from —NHAc and —NAc$_2$,
Q is COOCH$_3$, and
X is leaving group,
to yield a compound of general formula 2B

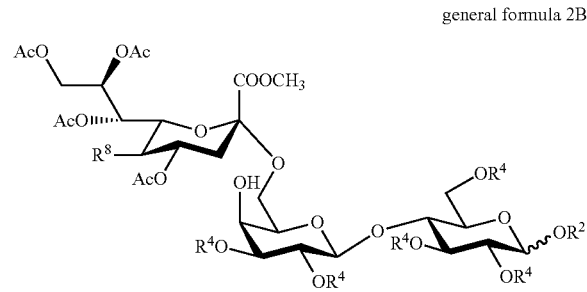

general formula 2B wherein $R^2$, $R^4$, and $R^8$ are as defined above,
b) the compound of general formula 2B is subjected to selective acidic deprotection to give a compound of general formula 2C

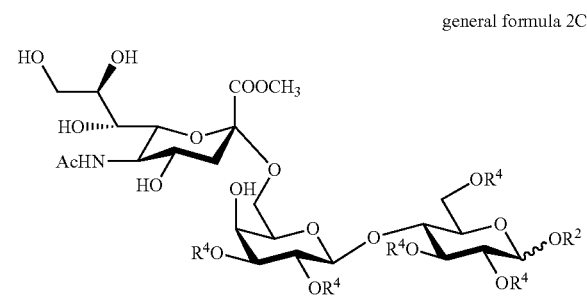

general formula 2C wherein R² and R⁴ are as defined above, followed by
a) base catalyzed transesterification reaction followed by basic hydrolysis, optional acidification and optional salt formation, or
b) basic hydrolysis, optional acidification and optional salt formation to give a compound of general formula 1 or salts thereof

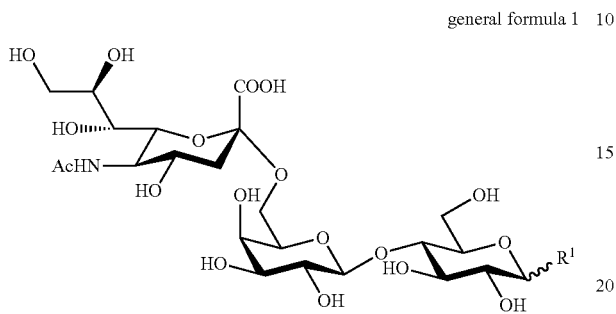

general formula 1 wherein R¹ is —O—R² and R² is as defined above, and
c) subsequently converting the compound of general formula 1 or salts thereof into 6'-O-sialyllactose or salts thereof.

2. The method according to claim 1, wherein R² is selected from benzyl, 4-methylbenzyl, 4-chlorobenzyl and 1-naphthylmethyl.

3. The method according to claim 1, wherein a compound of general formula 1 or salt thereof is subjected to catalytic reduction,
and when 6'-O-sialyllactose is obtained, it is optionally converted to a salt thereof, which salt of 6'-O-sialyllactose is optionally converted to another salt of 6'-O-sialyllactose.

4. The method according to claim 3, wherein R² is selected from benzyl, 4-methylbenzyl, 4-chlorobenzyl and 1-naphthylmethyl.

5. The method according to claim 1, wherein
the selective acidic deprotection is carried out in the presence of sulphuric acid on a compound of general formula 2B, wherein —OR² is in β, R² is selected from benzyl, 4-methylbenzyl, 4-chlorobenzyl and 1-naphthylmethyl, R⁴ is selected from isobutyryl, pivaloyl and optionally substituted benzoyl.

6. The method according to claim 1, in said method the glycosylation reaction comprises the use of a donor of general formulae 4A, 4B or 4C

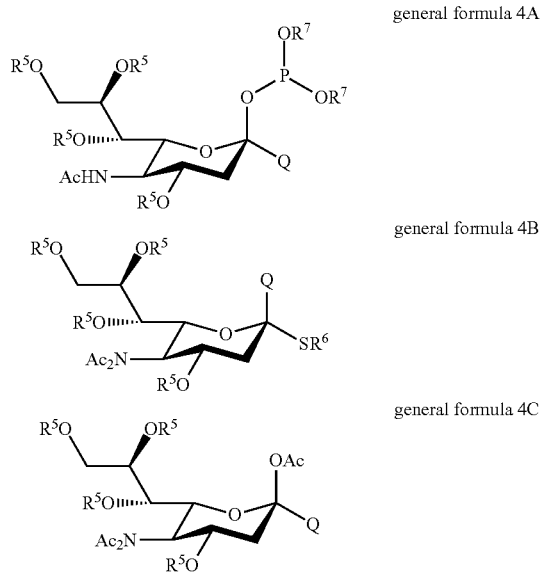

general formula 4A general formula 4B general formula 4C wherein R⁵ is acetyl,
R⁶ is selected form $C_{2-6}$ alkyl, $C_{3-6}$ cycloalkyl and optionally substituted benzyl,
R⁷ is substituted benzyl and
Q is —COOCH₃,
and of an acceptor of general formula 3A

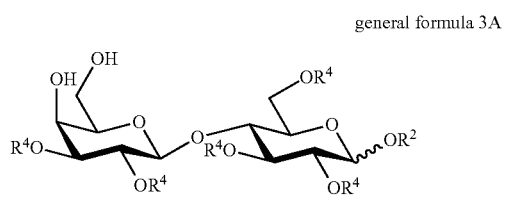

general formula 3A wherein R² is a group removable by catalytic hydrogenation, and
R⁴ is selected from optionally substituted acyl provided that acetyl is excluded.

7. The method according to claim 5, wherein R4 is benzoyl.

* * * * *